(12) United States Patent
Williams

(10) Patent No.: US 10,085,756 B2
(45) Date of Patent: Oct. 2, 2018

(54) ANVIL ASSEMBLY AND ANVIL ASSEMBLY DELIVERY SYSTEM

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 481 days.

(21) Appl. No.: 14/808,467

(22) Filed: Jul. 24, 2015

(65) Prior Publication Data

US 2017/0020527 A1    Jan. 26, 2017

(51) Int. Cl.
| | |
|---|---|
| *A61B 17/04* | (2006.01) |
| *A61B 17/10* | (2006.01) |
| *A61B 17/115* | (2006.01) |
| *A61B 17/11* | (2006.01) |
| *A61B 17/00* | (2006.01) |
| *A61B 90/00* | (2016.01) |
| *A61B 17/072* | (2006.01) |

(52) U.S. Cl.
CPC .... *A61B 17/1155* (2013.01); *A61B 17/00234* (2013.01); *A61B 17/1114* (2013.01); *A61B 17/072* (2013.01); *A61B 2017/00278* (2013.01); *A61B 2017/00292* (2013.01); *A61B 2017/00477* (2013.01); *A61B 2017/07257* (2013.01); *A61B 2090/037* (2016.02)

(58) Field of Classification Search
CPC ............. A61B 17/1155; A61B 17/1114; A61B 2017/07257; A61B 17/00234; A61B 2017/00278; A61B 2090/037
USPC ........................................... 227/175.1–182.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |

(Continued)

FOREIGN PATENT DOCUMENTS

| | | |
|---|---|---|
| CA | 908529 A | 8/1972 |
| DE | 1057729 B | 5/1959 |

(Continued)

*Primary Examiner* — Robert Long

(57) ABSTRACT

An anvil assembly suitable for trans-oral delivery includes an anvil head configured to receive a guide suture that is separable from the anvil assembly during a stapling procedure. An anvil delivery assembly includes the anvil assembly and a suture guide assembly secured to the anvil assembly.

18 Claims, 23 Drawing Sheets

(56) References Cited

U.S. PATENT DOCUMENTS

| | | |
|---|---|---|
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicola |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |

(56) References Cited

U.S. PATENT DOCUMENTS

| | | |
|---|---|---|
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicola |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |

(56) References Cited

U.S. PATENT DOCUMENTS

| | | | |
|---|---|---|---|
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2006/0265008 A1* | 11/2006 | Maruyama ......... A61B 17/0057 606/232 |
| 2006/0293700 A1* | 12/2006 | Dana ................ A61B 17/0467 606/148 |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0173865 A1* | 7/2007 | Oren ................. A61B 17/0467 606/148 |
| 2007/0270885 A1* | 11/2007 | Weinert ............. A61B 17/0469 606/139 |
| 2009/0012538 A1* | 1/2009 | Saliman ............ A61B 17/0491 606/145 |
| 2009/0082785 A1* | 3/2009 | Milliman ........... A61B 17/1155 606/139 |
| 2009/0082787 A1* | 3/2009 | Pang ................. A61B 17/0485 606/144 |
| 2009/0230170 A1* | 9/2009 | Milliman ........... A61B 17/0686 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0272783 A1* | 11/2009 | Crainich ........... A61B 17/0401 227/176.1 |
| 2010/0019016 A1 | 1/2010 | Edoga et al. |
| 2010/0023027 A1* | 1/2010 | Watschke .......... A61B 17/0469 606/144 |
| 2010/0038401 A1* | 2/2010 | Milliman ........... A61B 17/1114 227/175.1 |
| 2010/0051668 A1 | 3/2010 | Milliman et al. |
| 2010/0084453 A1 | 4/2010 | Hu |
| 2010/0121352 A1* | 5/2010 | Murray ............. A61B 17/0469 606/144 |
| 2010/0147923 A1 | 6/2010 | D'Agostino et al. |
| 2010/0154114 A1* | 6/2010 | Van Zeeland ........... E03C 1/23 4/689 |
| 2010/0163598 A1 | 7/2010 | Belzer |
| 2010/0176181 A1* | 7/2010 | Hessler .............. A61B 17/115 227/175.1 |
| 2010/0224668 A1 | 9/2010 | Fontayne et al. |
| 2010/0230465 A1 | 9/2010 | Smith et al. |
| 2010/0243711 A1* | 9/2010 | Olson .............. A61B 17/07207 227/181.1 |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0087247 A1* | 4/2011 | Fung ................. A61B 17/0469 606/148 |
| 2011/0114697 A1 | 5/2011 | Baxter, III et al. |
| 2011/0114700 A1 | 5/2011 | Baxter, III et al. |
| 2011/0118761 A1* | 5/2011 | Baxter, III ......... A61B 1/00087 606/148 |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0209300 A1* | 8/2012 | Torrie .............. A61B 17/0469 606/148 |
| 2012/0211544 A1* | 8/2012 | Olson ................ A61B 17/1155 227/176.1 |

(56) References Cited

U.S. PATENT DOCUMENTS

| | | |
|---|---|---|
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0030451 A1* | 1/2013 | Gross ................ A61B 17/0467 606/148 |
| 2013/0032628 A1 | 2/2013 | Li et al. |
| 2013/0056516 A1 | 3/2013 | Viola |
| 2013/0060258 A1 | 3/2013 | Giacomantonio |
| 2013/0079802 A1* | 3/2013 | Halac ................ A61B 17/0467 606/148 |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0116708 A1* | 5/2013 | Ziniti ................ A61B 17/0485 606/144 |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0039527 A1* | 2/2014 | Avelar ............ A61B 17/06166 606/144 |
| 2014/0151430 A1* | 6/2014 | Scheib ................ A61B 17/1155 227/175.1 |
| 2014/0303625 A1* | 10/2014 | Sholev ................ A61B 17/0482 606/80 |
| 2015/0366563 A1* | 12/2015 | Williams ............ A61B 17/068 227/175.1 |
| 2016/0000427 A1* | 1/2016 | Tu .................. A61B 17/0469 606/148 |
| 2016/0015380 A1* | 1/2016 | Sholev ................ A61B 17/0482 606/80 |
| 2016/0278810 A1* | 9/2016 | Richey ................ A61B 17/4241 |
| 2016/0302950 A1* | 10/2016 | Marmur .................. A61F 2/07 |
| 2017/0056017 A1* | 3/2017 | Vendely ............ A61B 17/07292 |
| 2017/0100119 A1* | 4/2017 | Baird .................. A61B 17/0469 |
| 2017/0100120 A1* | 4/2017 | Sauer ................ A61B 17/0482 |
| 2017/0215872 A1* | 8/2017 | Sauer ................ A61B 17/0469 |
| 2017/0216946 A1* | 8/2017 | Volpi .................. B65H 57/003 |
| 2017/0245861 A1* | 8/2017 | Clark, III ........ A61B 17/12013 |
| 2017/0290592 A1* | 10/2017 | Miller ............ A61B 17/12013 |
| 2017/0313460 A1* | 11/2017 | Kawada .................. B65C 7/00 |
| 2017/0319197 A1* | 11/2017 | Gross ................ A61B 17/0467 |
| 2017/0319198 A1* | 11/2017 | Meade ................ A61B 17/0625 |
| 2017/0325810 A1* | 11/2017 | Bonutti ............ A61B 17/0487 |
| 2017/0340891 A1* | 11/2017 | Boggs ................ A61N 1/37241 |
| 2017/0360427 A1* | 12/2017 | Ziniti ................ A61B 17/0487 |
| 2017/0360430 A1* | 12/2017 | Sauer ................ A61B 17/0469 |
| 2017/0367691 A1* | 12/2017 | Sakamoto ........ A61B 17/0469 |
| 2018/0014825 A1* | 1/2018 | Sholev ................ A61B 17/0642 |
| 2018/0028175 A1* | 2/2018 | Whittaker .......... A61B 17/0401 |
| 2018/0028179 A1* | 2/2018 | Bagaoisan ........ A61B 17/0057 |
| 2018/0036000 A1* | 2/2018 | Terada ................ A61B 17/0469 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

* cited by examiner

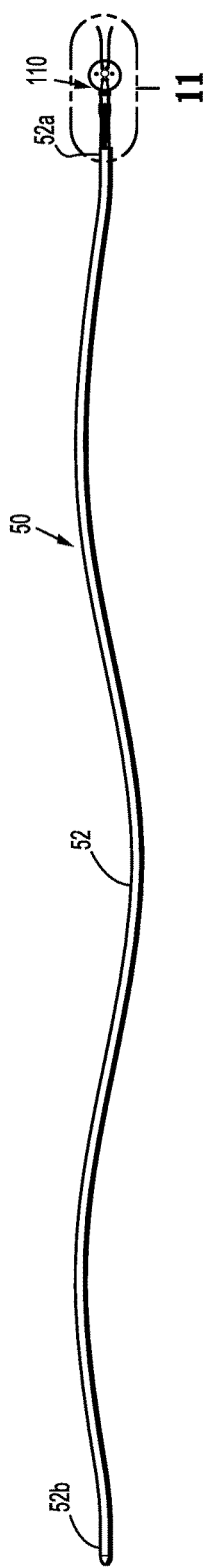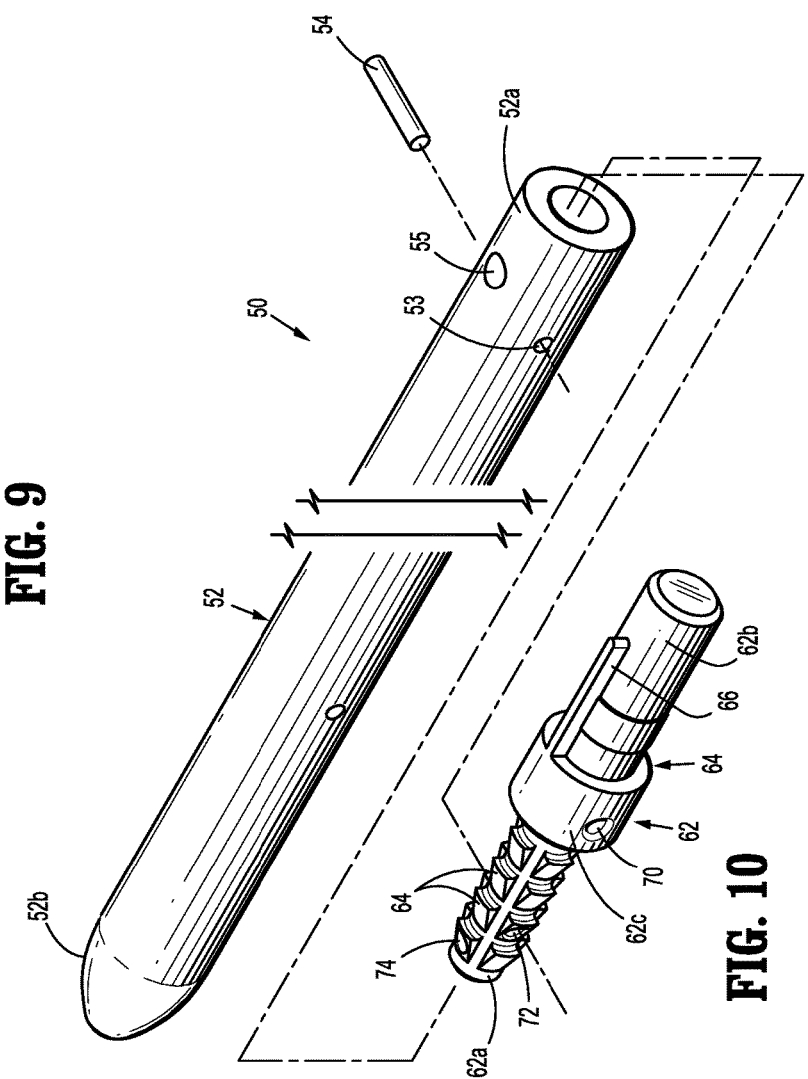
FIG. 9
FIG. 10

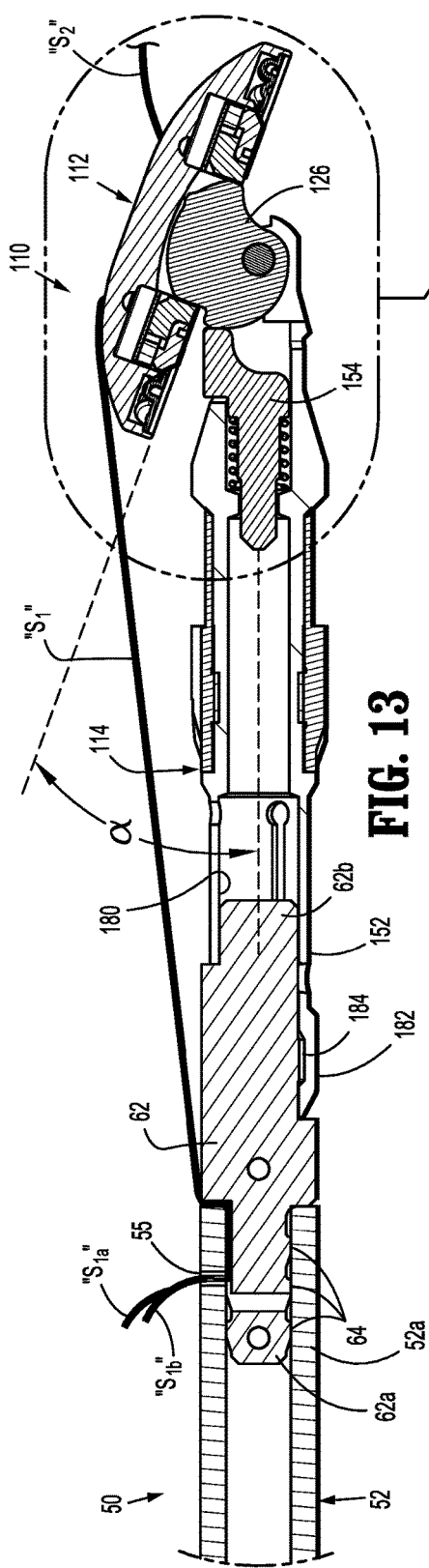

US 10,085,756 B2

ANVIL ASSEMBLY AND ANVIL ASSEMBLY DELIVERY SYSTEM

BACKGROUND

Technical Field

The present disclosure relates to an anvil assembly for use with a surgical stapling device. More particularly, the present disclosure relates to a delivery system for trans-oral delivery of the anvil assembly.

Background of Related Art

Trans-oral delivery systems for delivering an anvil assembly to a surgical site, e.g., the stomach, are known. In known delivery systems, a guide suture is threaded through one or more openings in the head of the anvil assembly to facilitate trans-oral insertion of the anvil assembly. The guide suture which include ends that remain external of the patient's mouth, may be used by the surgeon to dislodge the anvil assembly if it becomes stuck during trans-oral delivery and/or to retrieve the anvil assembly in the event of a patient emergency, e.g., cardiac arrest. Improved methods for securing the guide suture to an anvil assembly to facilitate detachment of the guide suture from the anvil assembly once the anvil assembly is delivered to the surgical site and/or the stapling procedure has been performed would be desirable.

SUMMARY

An anvil assembly is provided. The anvil assembly includes an anvil center rod and a head assembly pivotally secured to the anvil center rod. The head assembly includes a housing and a latch member mounted within the housing. The latch member is movable between a first position and a second position. The anvil assembly further includes a first suture received about the latch member. When the latch member is in the first position, the latch member is positioned to prevent separation of the first suture from the head assembly and when the latch member is in the second position, the latch member is positioned to allow separation of the first suture from the head assembly.

In embodiments, the head assembly includes a backup member supported within the housing. The backup member may be movable within the housing from a proximal position to a distal position. The backup member may include a retaining post configured to engage the latch member when the backup member is in the proximal position. The retaining post may define a cutout. The cutout may be aligned with the latch member when the backup member is in the distal position. The latch member may include a curved body portion for receiving the first suture thereabout.

In some embodiments, the housing defines an arcuate cutout. The latch member may enclose the cutout when the latch member is in the first position. The first suture may be retained within the cutout when the latch member is in the first position by the latch member. The head assembly may include a retainer member for maintaining the backup member in the proximal position. The retainer member may include a body and a frangible ring separable from the body to permit movement of the backup member from the proximal position to the distal position.

Another anvil assembly is provided. The anvil assembly includes an anvil center rod, and a head assembly pivotally secured to the anvil center rod. The head assembly includes a housing and a retaining member supported within the housing. The backup member is movable between a proximal position and a distal position. The anvil assembly further includes a first suture extending from the head assembly. When the backup member is in the proximal position of the retaining member, the backup member is positioned to prevent separation of the first suture from the head assembly and when the backup member is in the distal position, the backup member is positioned to allow separation of the first suture from the head assembly.

In embodiments, the head assembly includes a latch member mounted within the housing. The latch member may be movable within the housing from a first position to a second position. The backup member may include a retaining post configured to engage the latch member when the backup member is in the proximal position. The retaining post may define a cutout. The cutout may be aligned with the latch member when the backup member is in the distal position. The latch member may include a curved body portion for receiving the first suture thereabout. The housing may define an arcuate cutout. The latch member may enclose the cutout when the latch member is in the first position. The first suture may be retained within the cutout when the latch member is in the first position by the latch member. The head assembly may include a retainer member for maintaining the backup member in the proximal position. The retainer member may include a body and a frangible ring separable from the body to permit movement of the backup member from the proximal position to the distal position.

BRIEF DESCRIPTION OF THE DRAWINGS

Various embodiments of the presently disclosed anvil assembly and anvil assembly delivery system are disclosed herein with reference to the drawings wherein:

FIG. 9 is a top view of the anvil assembly of FIGS. 1-7 supported on an anvil delivery system;

FIG. 10 is an enlarged exploded view of the anvil delivery system of FIG. 9;

FIG. 13 is a cross sectional side view of the anvil assembly of FIGS. 1-7, in a pre-fired tilted position supported on the anvil delivery system of FIGS. 9-12;

FIG. 14 is an enlarged view of the indicated area of detail shown in FIG. 13;

DETAILED DESCRIPTION OF EMBODIMENTS

Figure 1:
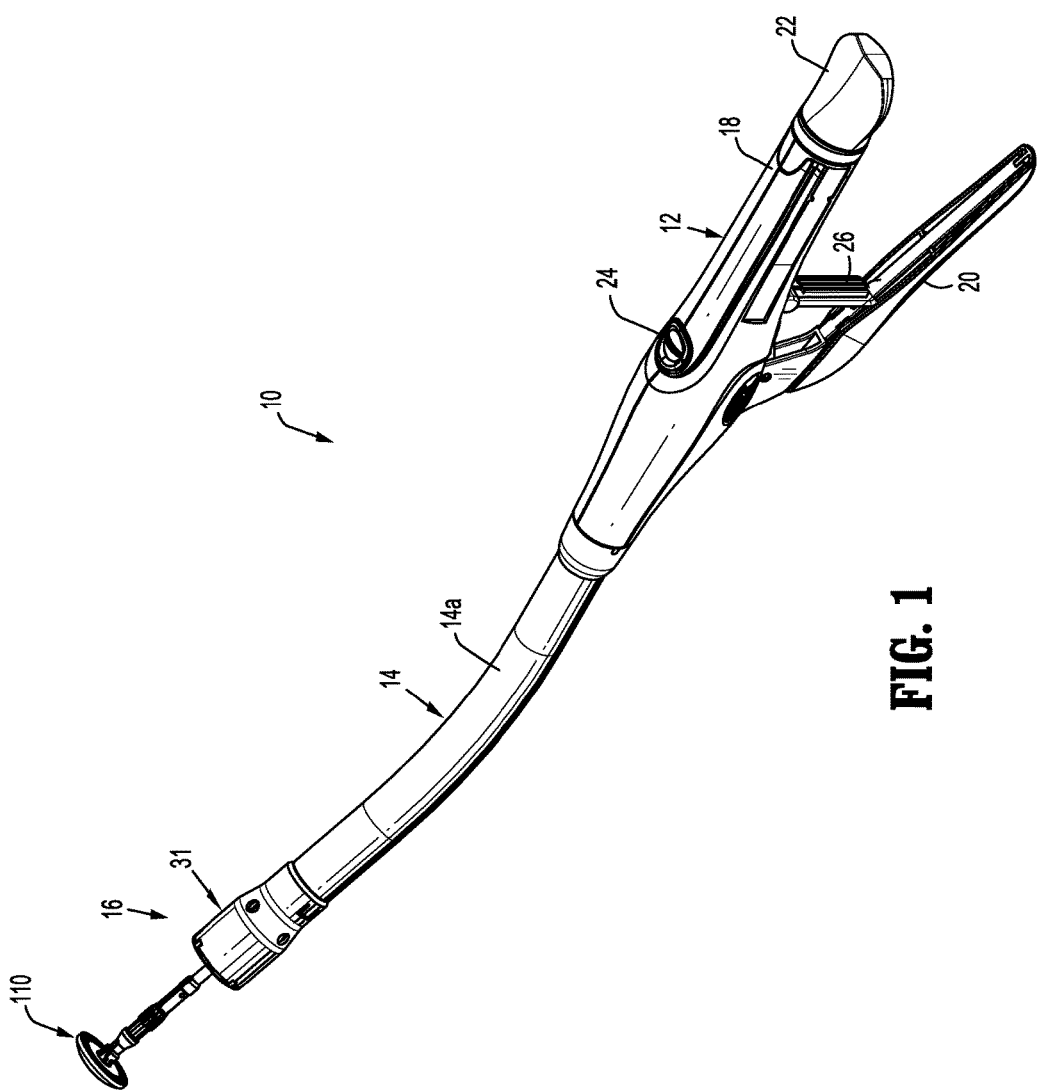
FIG. 1 is a perspective view of a surgical stapling device including an embodiment of an anvil assembly according to the present disclosure.
Figure 2:
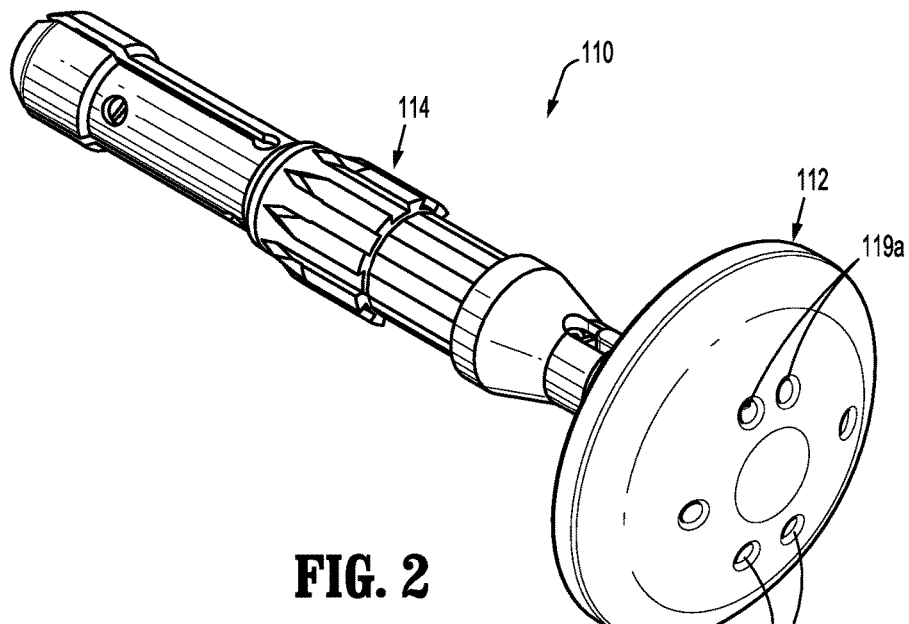
FIG. 2 is a first perspective side view of the anvil assembly of FIG. 1.

Embodiments of the presently disclosed anvil assembly delivery system will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

FIG. 1 illustrates an embodiment of a surgical stapling device configured for use with tilt anvil assemblies according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of the body portion 14 and the distal head portion 16 may also be varied to suit a particular surgical procedure.

With reference still to FIG. 1, the handle assembly 12 includes a stationary handle 18, a firing trigger 20, a rotatable approximation knob 22 and an indicator 24. A pivotally mounted trigger lock 26 is fastened to the handle assembly 12 and is manually positioned to prevent inadvertent firing of the stapling device 10. The indicator 24 is positioned on the stationary handle 18 and includes indicia, e.g., color coding, alpha-numeric labeling, etc., to identify to a surgeon whether the device is approximated and is ready to be fired. The head portion 16 includes an anvil assembly 110 and a shell assembly 31. For a more detailed discussion of the surgical stapler 10, please refer to commonly owned U.S. Pat. No. 7,364,060 to Milliman, the contents of which is incorporated herein by reference in its entirety.

Referring now to FIGS. 2-7, an anvil assembly according to an embodiment of the present disclosure is shown generally as anvil assembly 110. The anvil assembly 110 is shown in a non-titled position or operative position. The anvil assembly 110 includes a head assembly 112 and a center rod assembly 114. The head assembly 112 includes a post 116, a housing 118, a backup member or plate 120, a cutting ring 122, a cutting ring cover 123, an anvil plate 124, a spacer or washer 125, a cam latch member 126, and a retainer member 127. The post 116 is monolithically formed with and centrally positioned within the housing 118. Alternately, the housing 118 and the post 116 may be formed separately and fastened together using a known fastening technique, e.g., welding.

As will be discussed in further detail below, the housing 118 includes openings 119a, 119b sized and dimensioned to receive one or more sutures "S". During use, a first suture "$S_1$" (FIG. 9) is inserted through openings 119a and is used to retain the head assembly 112 in a retracted or first tilted position (FIG. 9) during insertion of the anvil assembly 110 within a patient. A second suture "$S_2$" (FIG. 9) is inserted through the openings 119b. The second suture "$S_2$" is configured to facilitate guiding the anvil assembly 110 trans-orally within a patient. During trans-oral insertion of the anvil assembly 110, the suture "$S_2$" extends from the mouth of patient, permitting the anvil assembly 110 to be retrieved trans-orally.

With reference still to FIGS. 2-7, the anvil plate 124 is supported in an outer annular recess 128 of the housing 118 and includes a plurality of staple deforming pockets 130 for receiving and deforming staples. At least one tab 124a extends radially outwardly from the anvil plate 124 and is received within a cutout 132 formed in an outer rim of the housing 118. The tab 124a and the cutout 132 function to align or properly position the anvil plate 124 within the annular recess 128 of the housing 118.

Figure 7:
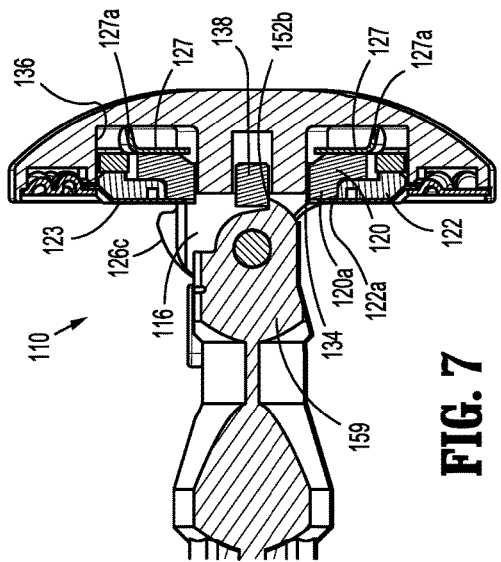
FIG. 7 is a cross-sectional side view of a distal end of the anvil assembly of FIGS. 1-6 taken along line 7-7 of FIG. 5.
Figure 6:
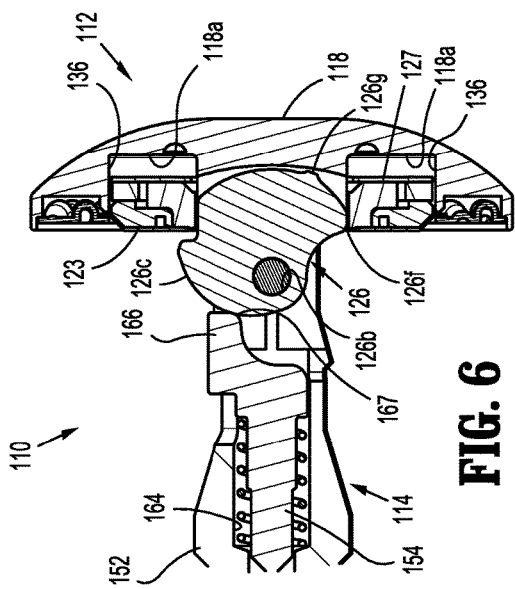
FIG. 6 is a cross-sectional side view of a distal end of the tilt anvil assembly of FIGS. 1-6 taken along line 6-6 of FIG. 5.
Figure 5:
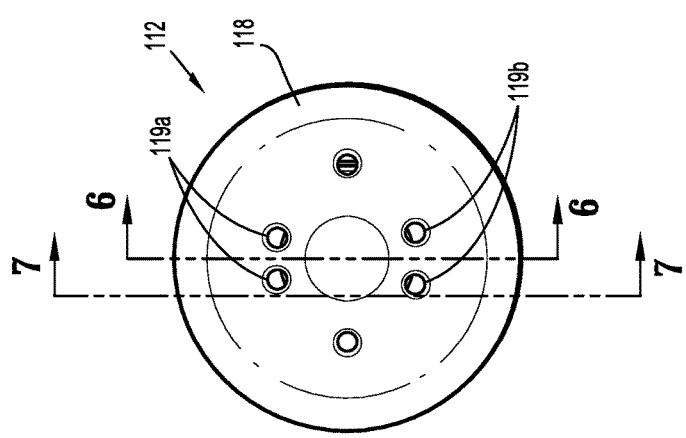
FIG. 5 is an end view of the anvil assembly of FIGS. 1-4.

With particular reference to FIGS. 6 and 7, the head assembly 112 will be described in detail. The backup plate 120 includes a central opening 134 which is positioned about the post 116 within an inner annular recess 136 of the housing 118 between the post 116 and the outer annular recess 128. The backup plate 120 includes a raised platform 120a. the cutting ring 122 includes an opening 122a having a configuration substantially the same as the platform 120a. Although the platform 120a is illustrated as having a circular shape, other configurations are envisioned, e.g., square, rectangular, triangular, etc. In one embodiment, the cutting ring 122 is formed from polyethylene and is fixedly secured to the backup plate 120 using, for example, an adhesive, to form a backup plate/cutting ring assembly. The backup plate 120 is formed from a hard material, e.g., a metal. Alternately other materials of construction may be used to construct the backup plate 120 and the cutting ring 122. Further, the backup plate 120 and the cutting ring 122, in the alternative, can be formed as a single or unitary structure.

Still referring to FIGS. 6 and 7, a cutting ring cover 123 is secured to an outwardly facing or proximal surface of the cutting ring 122 using, for example, an adhesive. In one embodiment, the cutting ring cover 123 is formed from a material or materials, having hardness greater than that of the cutting ring, e.g., mylar. In one embodiment, the cutting ring cover 123 includes two layers of mylar (not shown) which are joined together using an adhesive and a polypropylene coating. Alternately, the cutting ring 122 need not have a cover. The cutting ring 122 and the backup plate 120 are slidably mounted about the post 116. The backup plate 120 includes a pair of inwardly extending fingers 138 which will be described in further detail below.

With reference still to FIGS. 6 and 7, the retainer member 127 is positioned in the inner annular recess 136 between the backup plate 120 and a back wall 118a of the housing 118. In one embodiment, the retainer member 127 is annular and includes a plurality of deformable tabs 127a which engage a rear surface of the backup plate 120. The retainer member 127 prevents the backup plate 120 and the cutting ring 122 from moving or being pushed into the inner annular recess 136 of the housing 118 until a predetermined force sufficient to deform the tabs 127a has been applied to the backup plate/cutting ring assembly. The predetermined force can be close to but is less than the force applied by an annular cutting blade of a surgical stapling device when it engages, for example, the cutting ring of the anvil assembly 110. In one embodiment by way of example, the predetermined force is between about ten pounds and about ninety pounds and can be about thirty (30) pounds. When the predetermined force is reached, e.g., during cutting of tissue, the backup plate 120 is urged into the inner annular recess 136 and compresses the retainer member 127. It is envisioned that other crushable, deformable, collapsible or movement restricting members may be used to retain the backup plate/cutting ring assembly in a fixed position until a predetermined force has been applied to the backup plate/cutting ring assembly.

Turning back to FIG. 4, the anvil center rod assembly 114 includes a center rod 152, a plunger 154 and plunger spring 156. A first end of center rod 152 includes a pair of arms 159 which define a cavity 159a. Each arm 159 has a transverse throughbore 158 which is aligned with a central longitudinal axis of the center rod 152. Alternately, the throughbores 158 can be offset from the longitudinal axis of the center rod 152. The post 116 of the head assembly 112 is dimensioned to be positioned within the cavity 159a and also includes a transverse throughbore (not shown). A pivot member 162 pivotally secures the post 116 to the center rod 152 via the throughbores 158 such that the head assembly 112 may be pivotally mounted to the anvil center rod assembly 114.

Figure 3:
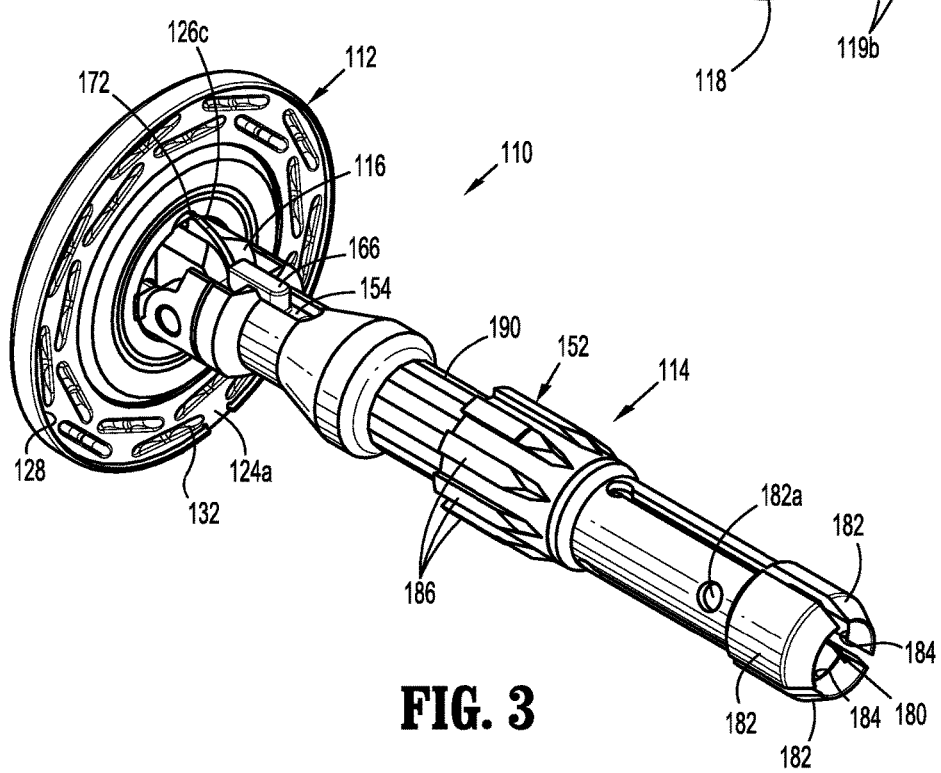
FIG. 3 is a second perspective side view of the anvil assembly shown in FIGS. 1 and 2.
Figure 8:
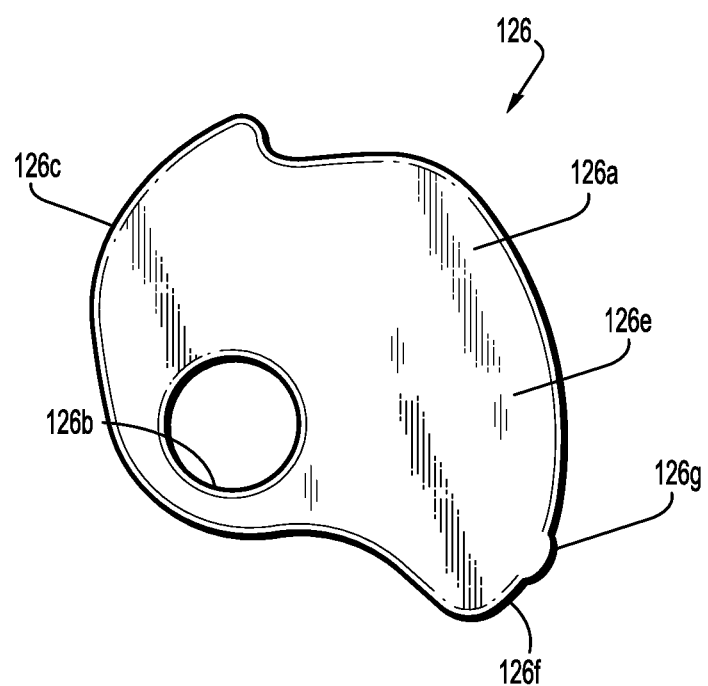
FIG. 8 is an enlarged side view of the cam latch member of the anvil assembly of FIGS. 1-7.
Figure 11:
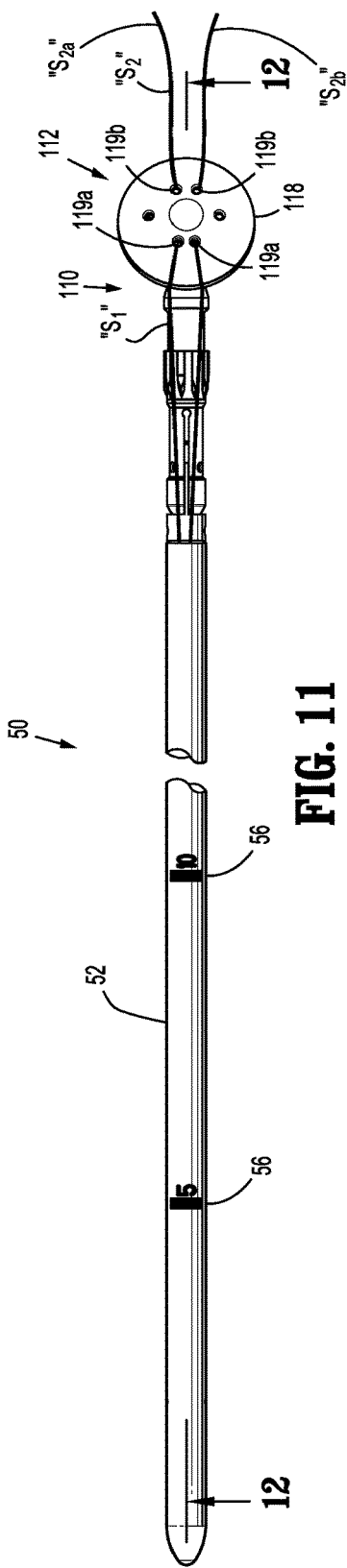
FIG. 11 an enlarged top view of the anvil delivery system of FIGS. 9 and 10, including the anvil assembly of FIGS. 1-7.
Figure 12:
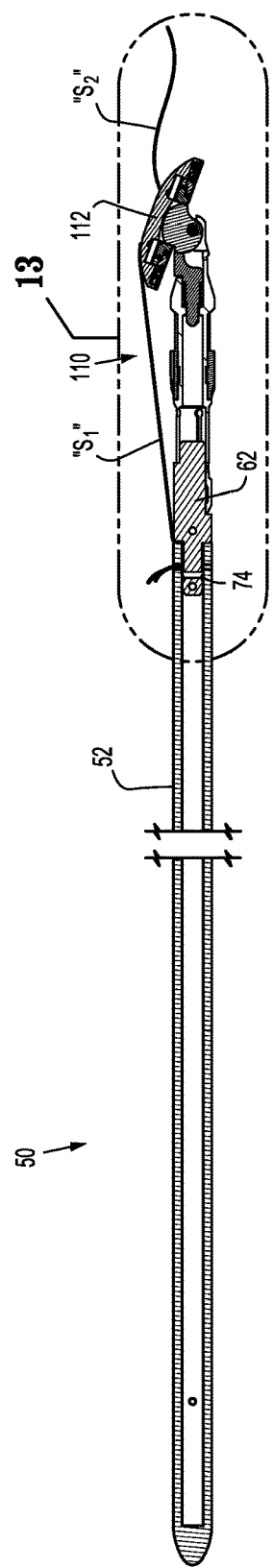
FIG. 12 is a cross-sectional side view of the anvil assembly and anvil assembly delivery system of FIG. 11 taken along lines 12-12 of FIG. 11.

Turning briefly to FIG. 8, the cam latch member 126 includes a body 126a having a throughbore 126b. The throughbore 126b is dimensioned to receive the pivot member 162 such that the cam latch member 126 is pivotally mounted within the transverse slot 172 (FIG. 3) of the post 116 about the pivot member 162. Referring now to FIGS. 3, 6 and 7, the cam latch member 126 includes a body portion 126c which extends partially from the transverse slot 172 of the post 116 and is positioned to be engaged by a finger 166 of the plunger 154. The body portion 126c is configured such that the distance between the surface of the body portion 126c and the throughbore 126b increase in a clockwise direction about the cam latch member 126. In this manner, the plunger 154 is able to move forward as the cam latch member 126 rotates in a clockwise direction. Additionally, this configuration of the body portion 126c permits the plunger 154 to be retracted as the cam latch member 126 rotates in a counter-clockwise direction. The cam latch member 126 also includes an edge 126f, including a tab 126b. A leading portion of edge 126f is configured to be urged into engagement with an inner periphery 120b of the backup plate 120 by an engagement finger 166 of the plunger 154 when the head assembly 112 is in its non-tilted or operative position. The tab 126g is configured to engage the backwall 118a of the housing 118 to prevent the cam latch member 126 from rotating counter-clockwise relative to the housing 118.

With reference to FIG. 6, the plunger 154 is slidably positioned in a bore 164 formed in the first end of center rod 152. The finger 166 of the plunger 154 is offset from the pivot axis of head assembly 112 and is biased into engagement with the body portion 126c of the cam latch 126. Engagement of the finger 166 with the body portion 126c of the cam latch member 126 presses a leading portion of the edge 126f against an inner periphery of the back plate 120 to urge the head assembly 112 to an operative or non-tilted position on the center rod 152.

Turning to FIG. 7, in the pre-fired operative position of the head assembly 112, i.e. when the head assembly 112 has been pivoted to its non-tilted position, the fingers 138 formed on the backup plate 120 engage the protrusions 152b adjacent the top surface 152a of the center rod 152 to prevent the head assembly 112 from pivoting about the pivot member 162. The head assembly 112 may be tilted α degrees (FIG. 13) relative to the anvil center rod assembly 114 in the pre-fired tilted position. In one embodiment, the head assembly 112 is tilted about seventy degrees (70°) in its pre-fired tilted position; however it should be understood that tilting the head assembly 112 to other degrees is also contemplated. Titling of the head assembly 112 relative to the anvil center rod assembly 114 causes the body portion 126c of the cam latch member 126 to engage the finger 166 of the plunger 154. As the cam latch member 126 rotates with the tilting of the head assembly 112, the plunger 154 is refracted within the bore 164 of the anvil center rod assembly 114, thereby compressing the spring 156. In this manner, the finger 166 of the plunger 154 is distally biased against the body portion 126c of cam latch member 126.

Figure 4:
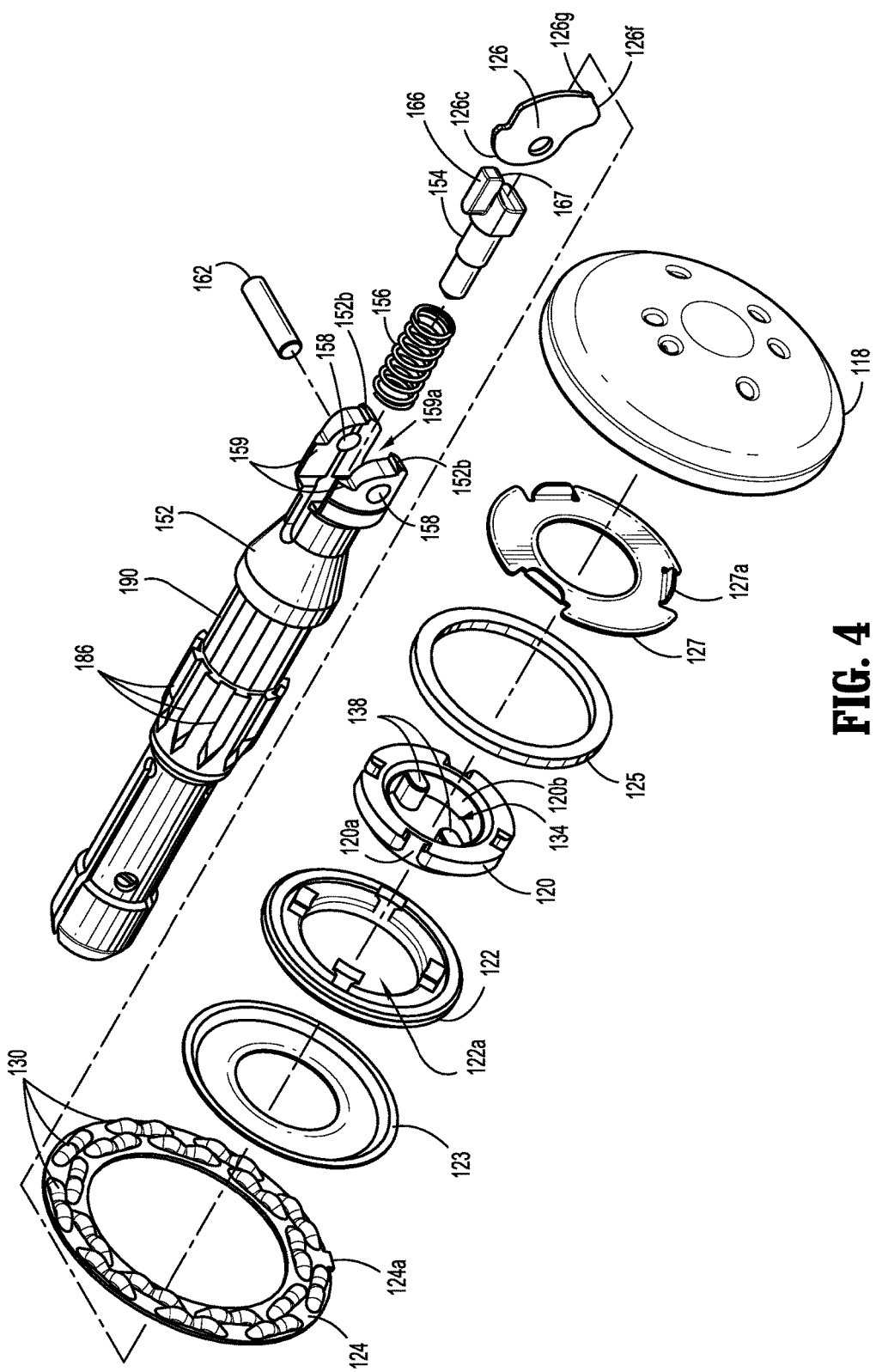
FIG. 4 is an exploded side view of the anvil assembly of FIGS. 1-3.
Figure 18:
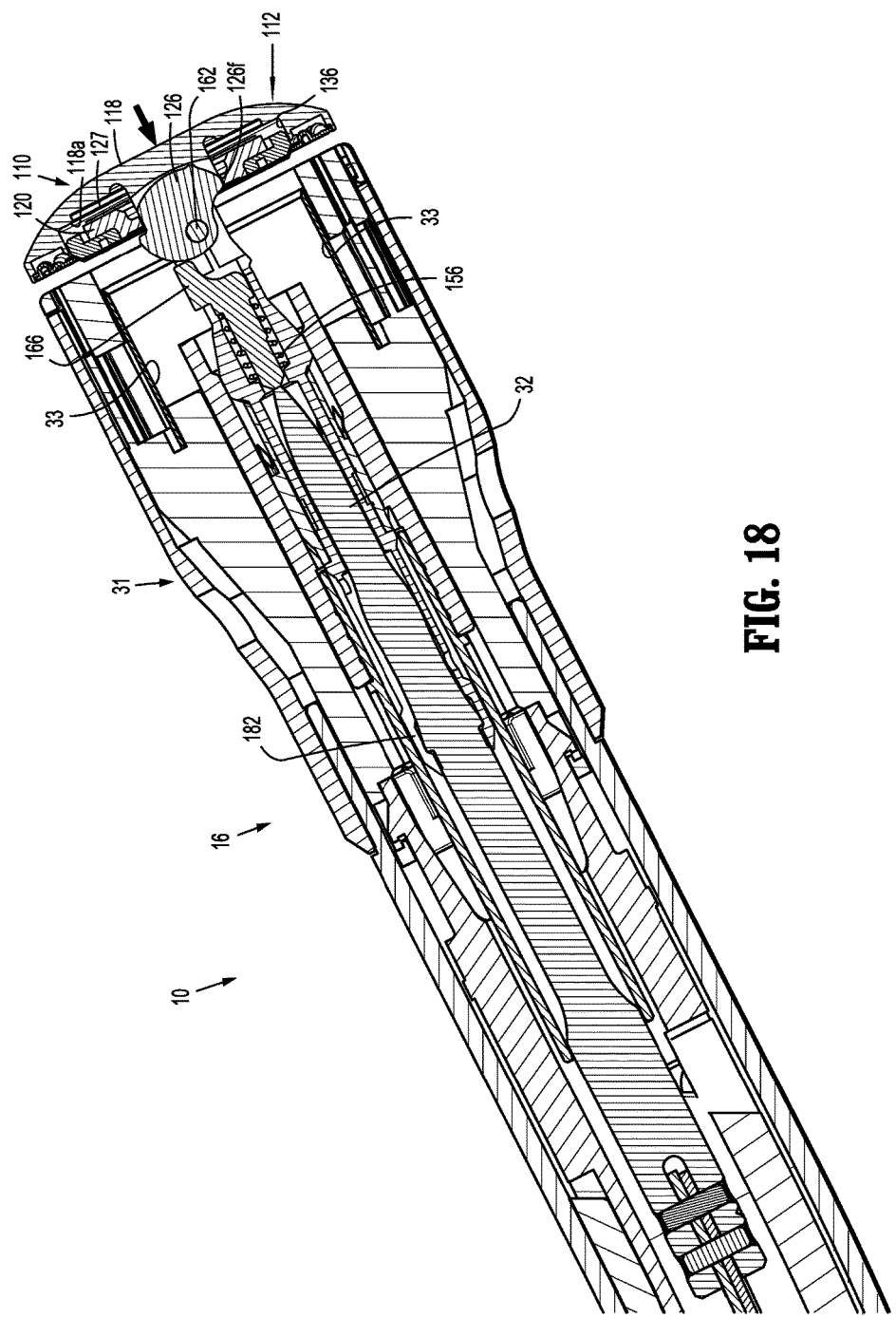
FIG. 18 is an enlarged cross-sectional side view of the distal head portion of the surgical stapling device of FIG. 1 and the anvil assembly of FIGS. 1-7 in a pre-fired non-tilted operative position.
Figure 19:
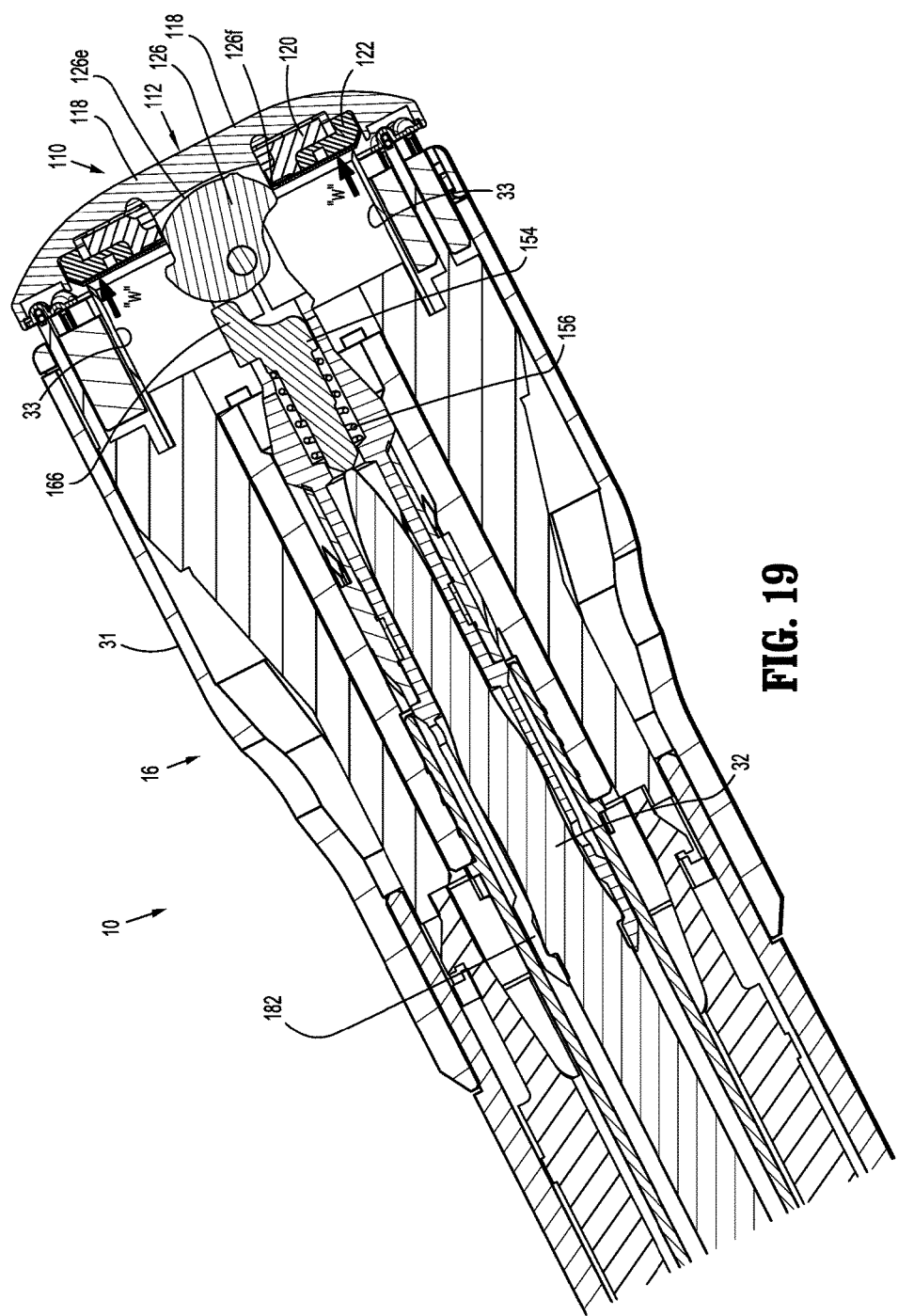
FIG. 19 is an enlarged cross-sectional side view of the distal head portion of the surgical stapling device of FIG. 1 and the anvil assembly of FIGS. 1-7 in a post-fired non-titled operative position.
Figure 20:
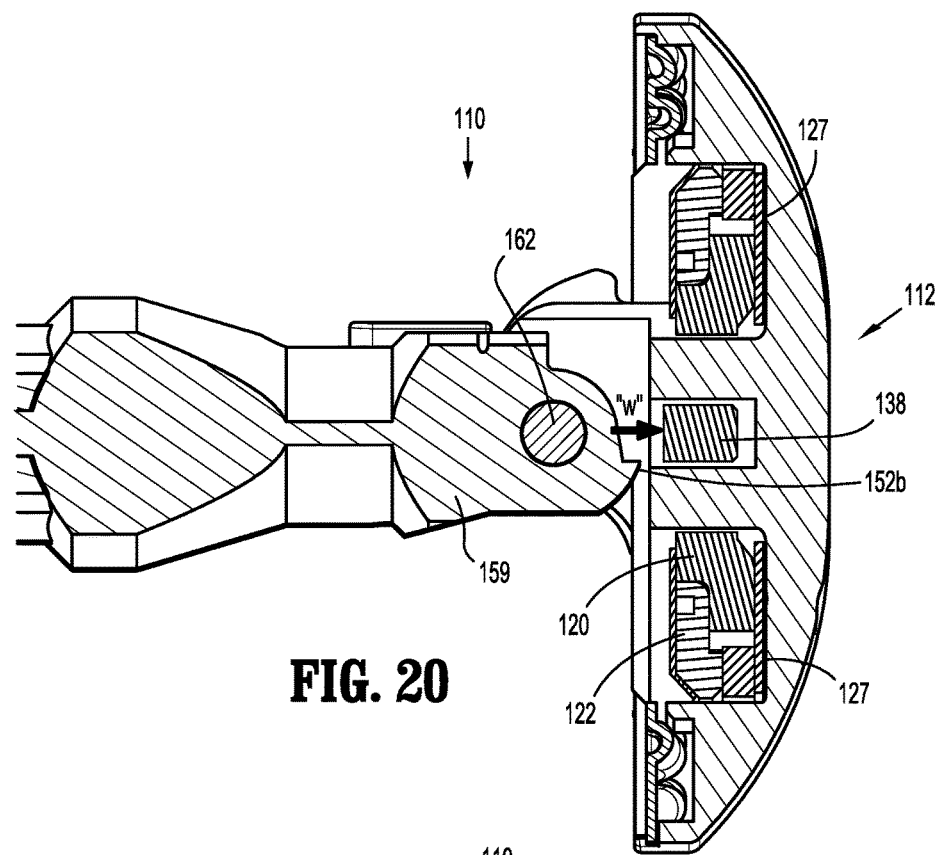
FIG. 20 is an enlarged cross-sectional side view of the distal end of the anvil assembly of FIGS. 1-7 in the post-fired operative position.
Figure 21:
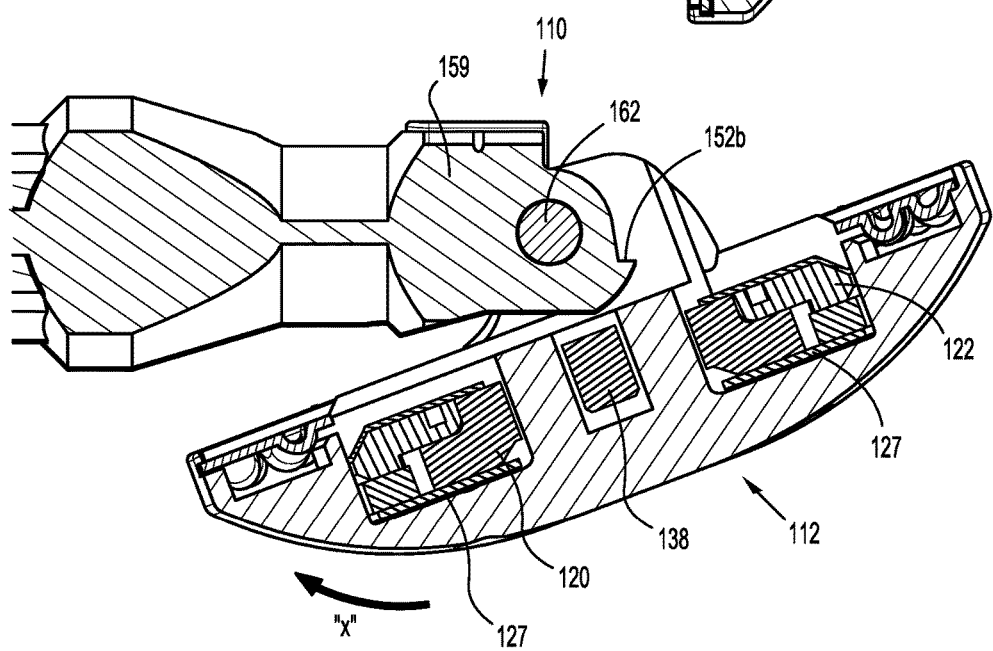
FIG. 21 is an enlarged cross-sectional side view of the distal end of the anvil assembly of FIGS. 1-7 in a post-fired tilted position.

With reference to FIGS. 3 and 4, a second end of the center rod 152 includes a bore 180 defined by a plurality of the flexible arms 182. The flexible arms 182 each include an opening 182a dimensioned to receive a projection formed on or connected to a shell assembly 31 (FIG. 18). Alternatively, the openings 182a may be configured to receive a suture for permitting retrieval of the anvil assembly 110. The proximal ends of each of the flexible arms 182 include an internal shoulder 184 dimensioned to releasably engage the shell assembly 31 of the surgical stapling device 10 to secure the anvil assembly 110 to the surgical stapling device 10. A plurality of splines 186 are formed about the center rod 152. The splines 186 function to align the anvil assembly 110 with the staple holding portion of the surgical stapling device 10. The center rod 152 also includes an annular recessed portion 190 to facilitate grasping of the anvil assembly 110 by a surgeon with a grasper (not shown). The recessed portion 190 may include a roughened or knurled surface or an overmold to facilitate grasping of the anvil assembly 110.

With reference now to FIGS. 9-12, a system for delivering the anvil assembly 110 within a patient is shown generally as anvil delivery system 50. The anvil delivery system 50 includes a flexible tube 52 and an adapter 62. The flexible tube 52 includes an open end 52a. The adapter 62 and the anvil assembly 110 are supported on the open end 52a of the flexible tube 52. The open end 52a of the flexible tube 52 includes a throughbore 53 extending therethrough configured to receive a locking pin 54. The open end 52a further includes an opening 55. The closed end 52b of the flexible tube 52 is configured for trans-orally receipt in a patient. The flexible tube 52 may include markings or other gradations 56 along the length thereof to indicate to a surgeon how much of the flexible tube 52 has been received within the patient during insertion and/or to indicate the length of the flexible tube 52 remaining in the patient upon removal.

With particular reference to FIG. 10, the adapter 62 includes a first end 62a configured to be received within the open end 52a of the flexible tube 52 and a second end 62b configured to be received with in the bore 180 formed in the center rod 152 of the anvil assembly 110. The first end 62a includes a series of annular rings 64 configured to frictionally retain the first end 62a of the adapter 62 within the open end 52a of the flexible tube 52. The second end 62b of the adapter 62 includes a longitudinal guide member 66 configured to be received between the flexible arms 182 formed in the center rod 152 of the anvil assembly 110. In addition, the second end 62b of the adapter 62 is sized to allow the center rod 154 of the anvil assembly 110 to freely slide into and off of the second end 62b of the adapter 62. The adapter 62 further includes a first throughbore 70 formed in a central hub portion 62c as well as second and third throughbores 72, 74 formed in the first end 62a. The first throughbore 72 is configured to align with the throughbore 53 formed in the open end 52a of the flexible tube 52 and is sized to receive the locking pin 54.

With particular reference now to FIGS. 10, 13 and 14, the anvil assembly 110 is supported on the anvil delivery system 50. Securing the anvil assembly 110 to the anvil delivery system 50 requires that the first suture "S$_1$" is thread through the openings 119a formed on the head assembly 112 such that the first and second ends "S$_{1a}$", "S$_{1b}$" of the suture "S$_1$" are positioned on opposites of the center rod 152. Next, the second end 62b of the adapter 62 is positioned within the throughbore 180 of the center rod 152 such that the longitudinal guide 66 is received between two of the arm members 182. Each of the first and second ends "S$_{1a}$", "S$_{1b}$" of the suture "S$_1$" is inserted through the opening 55 formed in the open end 52a of the flexible tube 52. The head assembly 112 is then rotated to a first tilted position while first and second ends "S$_{1a}$", "S$_{1b}$" of suture "S$_1$" are pulled through the opening 55. The first end 62a of the adapter 62 is then inserted into the open end 52a of the flexible member 52. The frictional contact between the annular rings 64 of the first end 62a of the adapter 62 and an inner surface of the flexible tube 52 secures the adapter 62 to the flexible tube 52 and prevents the first suture "S$_1$" from loosening. It is envisioned that more than one suture may be used to secure the head assembly 112 in a pre-fired tilted position.

Figure 15:
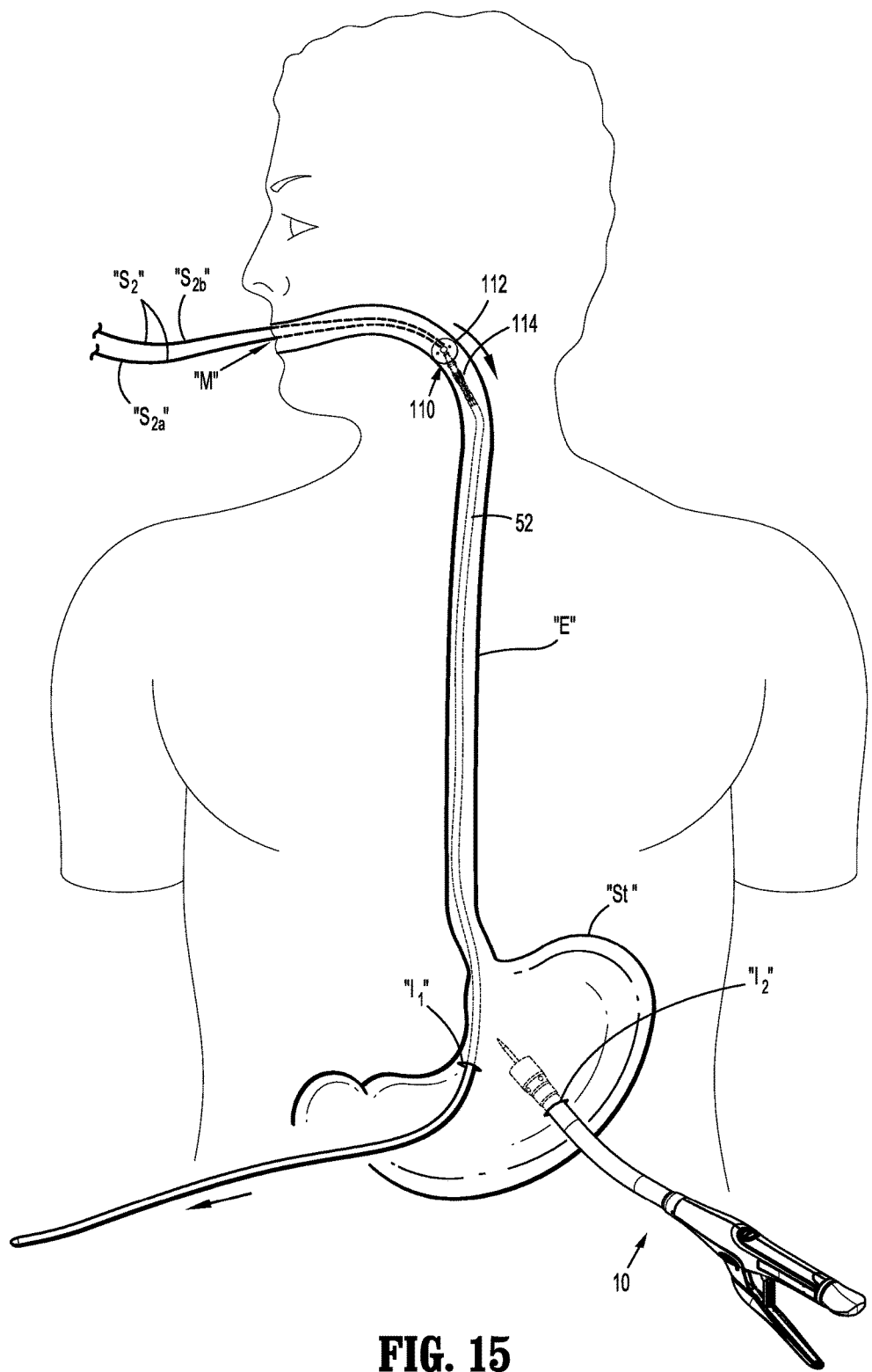
FIG. 15 is an illustration of the anvil assembly and anvil delivery system of FIGS. 11 and 12 being inserted trans-orally into a patient.

With reference now to FIG. 15, a method for delivering the anvil assembly 110 to a surgical site within a patient will be described. In one method, the anvil assembly 110 is provided in the first tilted position supported on the anvil delivery system 50 and ready for delivery. Alternatively, a clinician secures the anvil assembly 110 to the anvil delivery system 50 as discussed above. Once the anvil assembly 110 has been secured to the flexible tube 52, the surgeon inserts the closed end 52b of the flexible tube 52 in the patient's mouth "M" and moves the closed end 52b along with the flexible tube 52 down through esophagus "E" to a surgical site, i.e., the stomach "St".

After insertion, the surgeon then makes a first incision "I$_1$" at the surgical site (stomach "St" as shown) to create an inner access to the closed end 52b of the flexible tube 52 and then pulls the open end 52b of the flexible tube 52 through the first incision "I$_1$". In some procedures it may be beneficial to pull the flexible tube 52 through the incision "I$_1$" until the center rod 152 of the anvil assembly 110 advances through the first incision "I$_1$". When the anvil assembly 110 is properly positioned at the surgical site, the surgeon releases the anvil delivery system 50 from the anvil assembly 110 by cutting the suture "S$_1$" and separating the anvil assembly 110 from the second end 62b of the adapter 62. The flexible tube 52 (with the fitting 62) may then be pulled from the body through the first incision "I$_1$".

Severing of the suture "S$_1$" permits the plunger 154 to extend from within the bore 164, thereby causing the finger 166 to engage the body portion 126c of the cam latch member 126. Rotation of the cam latch member 126 causes the edge 126f of the cam latch member 126 to move into engagement with the inner periphery of the backup plate 120, thereby urging the head assembly 112 to return to a non-tilted operative position. Additionally, the distal end of the stapling device 10 may be configured to engage the finger 166 of the plunger 154 as the anvil assembly 110 is attached to the surgical stapling device 10. In this manner, the distal end of the surgical stapling device 10 urges the plunger 154 distally, thereby ensuring the rotation of the head assembly 112 to a non-tilted position.

With particular reference to FIG. 15, in one method, a second incision "I$_2$" is then formed at the surgical site such that the distal head portion 16 of surgical stapling device 10 may be received therethrough. Alternatively, the distal head portion 16 of the surgical stapling device 10 may be received through the first incision "I$_1$" once the anvil deliver system 50 has been removed from the first incision "I$_1$".

Figure 16:
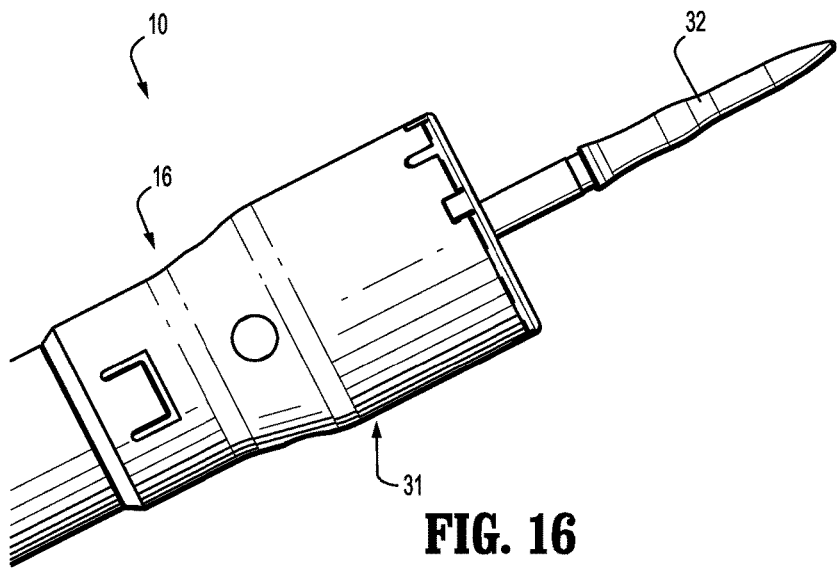
FIG. 16 is an enlarged side view of the distal head portion of the surgical stapling device of FIG. 1 with the anvil assembly removed.
Figure 17:
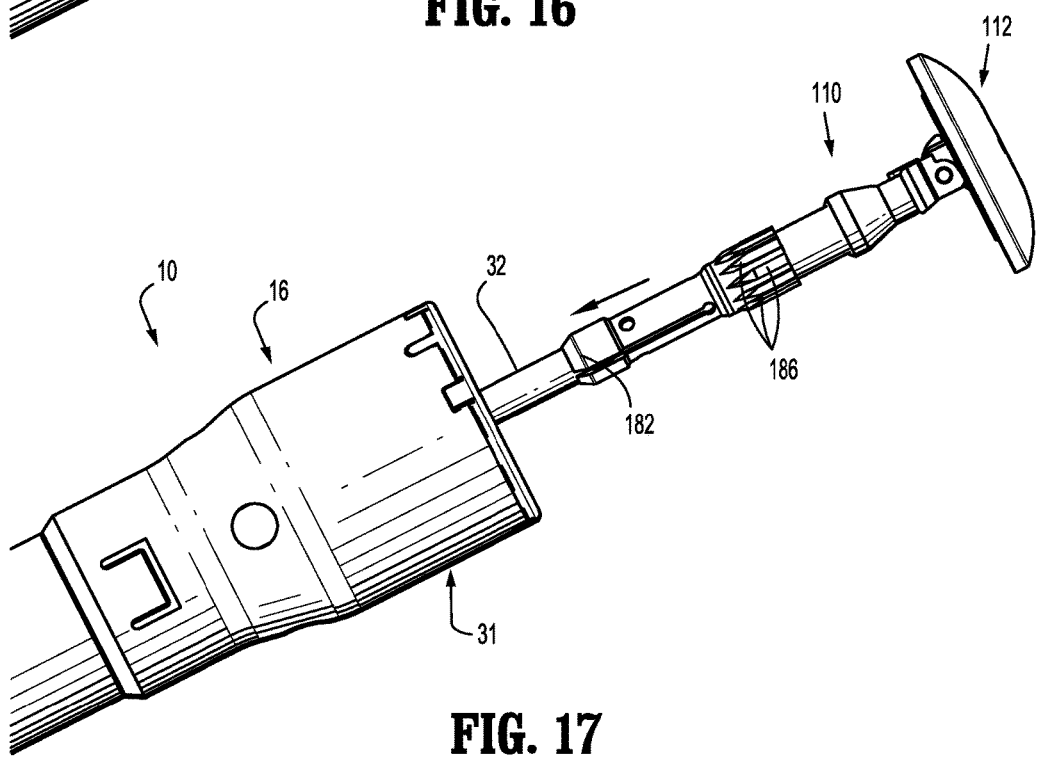
FIG. 17 is an enlarged side view of the distal head portion of the surgical stapling device of FIG. 1 with the anvil assembly of FIGS. 1-7 received thereon.

Turning briefly to FIGS. 16 and 17, the anvil assembly 110 is operably received on an anvil retainer 32 extending from the shell assembly 31 formed on a distal end of the surgical stapling device 10. Once the anvil assembly 110 is received on the surgical stapling device 10, the surgical stapling device 10 operates in the manner discussed in the '060 patent.

The operation of the anvil assembly 110 will now be described with reference to FIGS. 18-23. When the anvil assembly 110 is in its pre-fired non-tilted position, the backup plate 120 is spaced from the backwall 118a of the housing 118 by the retainer 127 and the protrusions 152b of the center rod 152 engage the fingers 138 of the backup plate 120 to prevent tilting of the head assembly 112 about the pivot member 162. The finger 166 of the plunger 154 is urged by the spring 156 into engagement with the body portion 126c of the cam latch member 126 to urge the cam latch member 126 in a clockwise direction, about the pivot member 162 such that the edge 126f of the cam latch member 126 engages the inner periphery 120b of the backup member 120.

Figure 22:
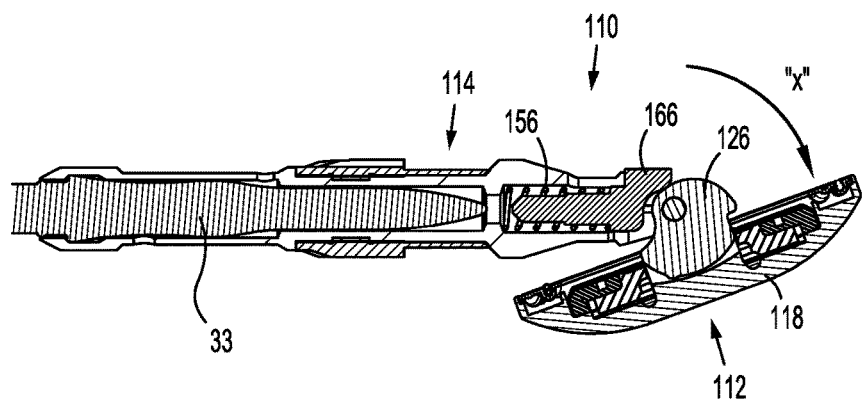
FIG. 22 is a cross-sectional side view of the anvil assembly of FIGS. 1-7 in a post-fired tilted position supported on an anvil retainer of the surgical instrument of FIG. 1.
Figure 22A:
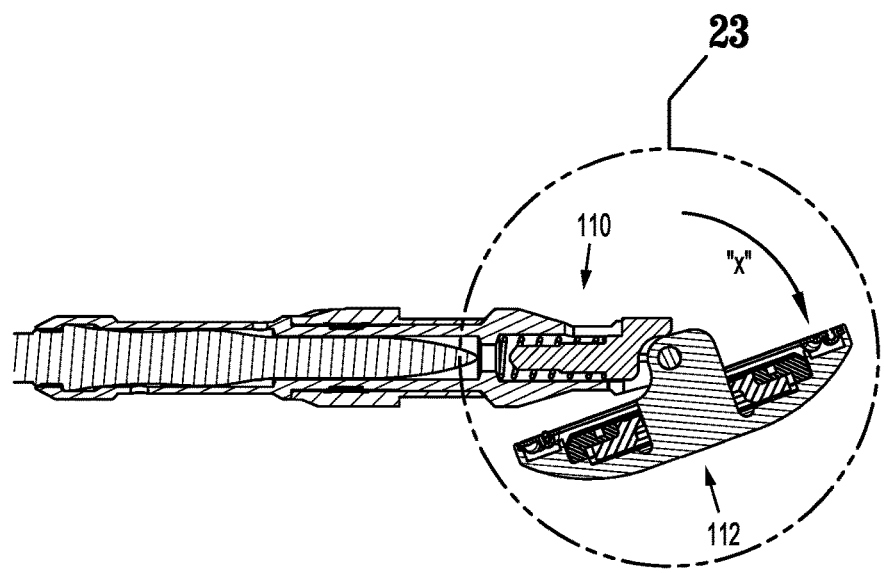
FIG. 22A is another cross-sectional side view of the anvil assembly of FIGS. 1-7 in a post-fired tilted position supported on an anvil retainer of the surgical instrument of FIG. 1
Figure 23:
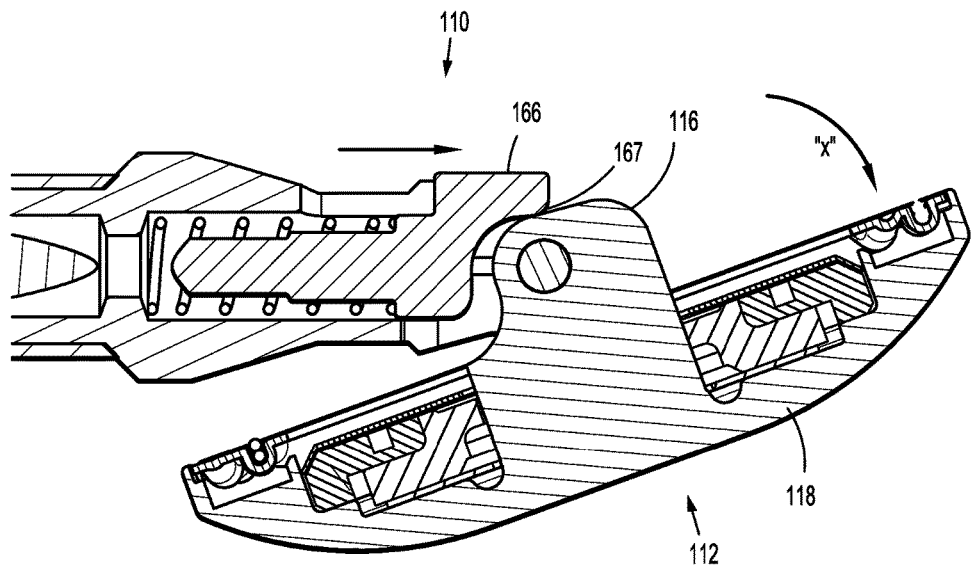
FIG. 23 is an enlarged view of the indicated area of detail shown in FIG. 22A.
Figure 24:
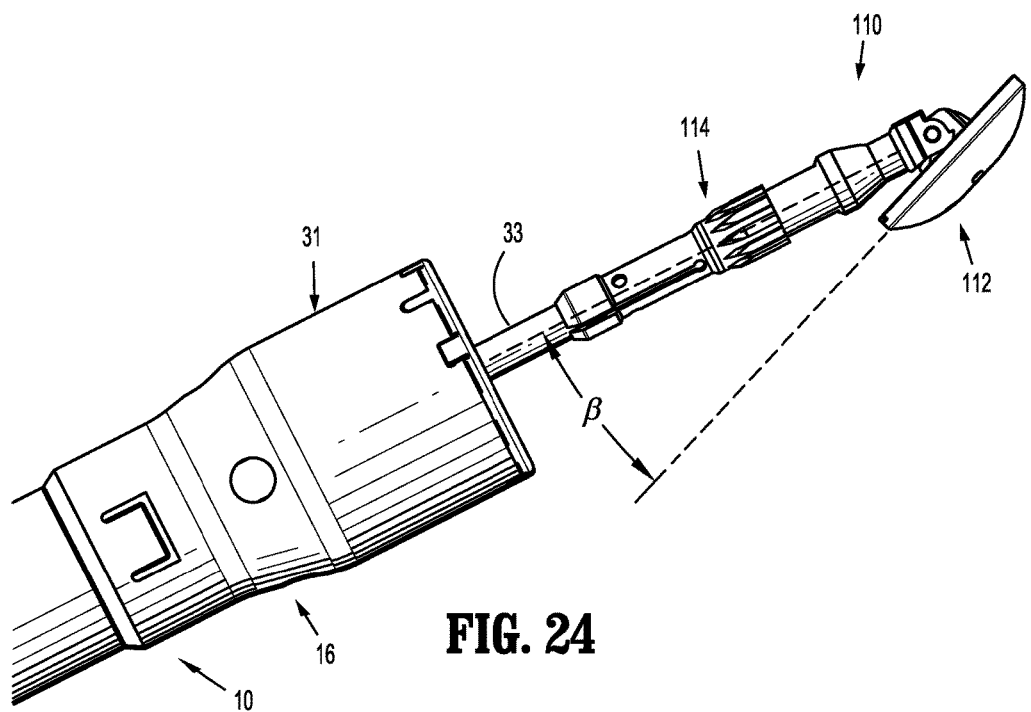
FIG. 24 is a side view of the anvil assembly of FIG. 22 supported on the anvil retainer of the surgical stapling device of FIG. 1.

The firing of the surgical stapling device 10 causes a knife blade 33 (FIG. 19) of the surgical stapling device 10 to engage the cutting ring 122 to move the cutting ring 122 and backup plate 120 into annular recess 136 of housing 118 of the head assembly 112. Arrows "W" in FIG. 19 indicate how cutting ring 122 and backup plate 120 move as a result of the firing of surgical stapling device 10. When such movement occurs, deformable tabs 127a of retainer 127 are deformed against backwall 118a of housing 118 and fingers 138 of backup member 120 move away from protrusions 152b of center rod 152. Further, inner periphery 120b of backup plate 120 moves past edge 126f of cam latch member 126 such that cam latch member 126 is urged to pivot about pivot member 162 in the direction indicated by arrow "X" in FIG. 21 by plunger 154 to a position in which body portion 126d is positioned in front of and engages backup plate 120. Engagement of plunger 154 with cam latch member 126 urges the head assembly 112 to a second tilted position (FIGS. 22 and 23). It is noted that the head assembly 112 will not immediately tilt upon firing of surgical stapling device 10 because, upon firing, the head assembly 112 is in an approximated position, i.e., the head assembly 112 is in close alignment with shell assembly 31 of stapling device 10, and, therefore, does not provide room for head assembly 112 to pivot. As such, the head assembly 112 will only begin to tilt when anvil assembly 110 and shell assembly 31 of surgical stapling device 10 are being unapproximated.

As the head assembly 112 pivots towards its forward or second tilted position, the finger 166 of the plunger 154 maintains the curved surface 126e of the cam latch member 126 in contact with the backup plate 120 to prevent the backup plate 120 from sticking to the knife blade 33 (FIG. 19) as the knife blade 33 is retracted. It is noted that the curved surface 126e of the cam latch member 126 is configured to eliminate any gap and ensure contact between the curved surface 126e of the cam latch member 126 and the backup plate 120 to hold the backup plate 120 in place during and after the knife blade 33 is retracted such that the cutting ring and backup plate assembly stay in their correct position during continued tilting of the anvil assembly 112. The anvil assembly 110 is configured such that the anvil head assembly tilts to a forward or second tilted position β degrees (FIG. 23) relative to the center rod assembly 114. In one embodiment, the head assembly 112 is tilted about seventy degrees (70°) to its second tilted position such that the total pivoting movement of the head assembly 112 from the retracted or first tilted position to the forward or second tilted position is about one-hundred and forty degrees (140°). It should, however, be noted that the tilting of the head assembly 112 to other degrees is also contemplated.

As described above, the anvil assemblies of the present disclosure are configured to be delivered to a surgical site, e.g., the stomach "St" (FIG. 15), trans-orally. During trans-oral delivery of the anvil assemblies, a retaining suture, i.e., first suture "$S_1$", retains the head assembly of the anvil assembly in a first tilted position and a proximal guide suture, i.e., the second suture "$S_2$", which includes the first and second ends "$S_{2a}$", "$S_{2b}$" that remain external of the patient's mouth "M", permits the surgeon to dislodge or retrieve the anvil assembly 110 from the patient during trans-oral delivery.

As described above and with reference to FIG. 11, the second suture "$S_2$" is threaded through the openings 119b in the housing 118 of the head assembly 112 of the anvil assembly 110. Detaching the second suture "$S_2$" from the anvil assembly 110 requires pulling on the first end "$S_{2a}$" of the second suture "$S_2$" such that the second end "$S_{2b}$" of the second suture "$S_2$" travels from a location externally of the patient's mouth "M" (FIG. 15) where it is accessible by the surgeon, through the patient's mouth "M" and upper gastrointestinal (GI) tract, e.g., esophagus "E" and stomach "St" (FIG. 15) (collectively referred to as the patient's body lumen) and through the openings 119b in the housing 118 of the head assembly 112 of the anvil assembly 110 before having to travel back through the upper GI tract and out the patient's mouth "M".

With reference to FIGS. 25-37, an anvil assembly according to another embodiment of the present disclosure is shown generally as anvil assembly 210. The anvil assembly 210 is substantially similar to the anvil assembly 110 described hereinabove and will only be described in detail as relates to the differences therebetween. The anvil assembly 210 includes a head assembly 212 and a center rod assembly 214.

Figure 25:
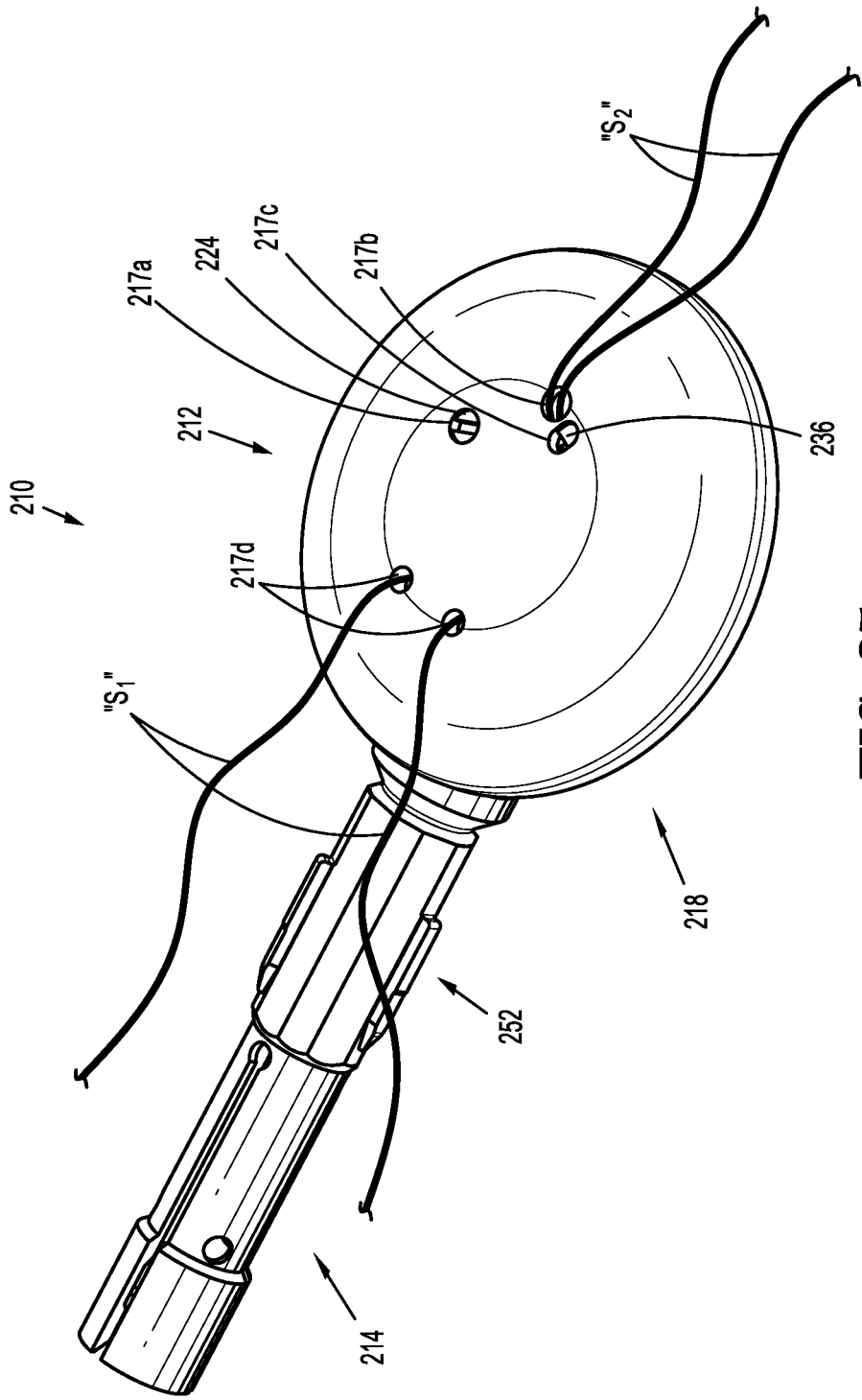
FIG. 25 is a perspective top view of an anvil assembly according to another embodiment of the present disclosure in the first tilted position.
Figure 26:
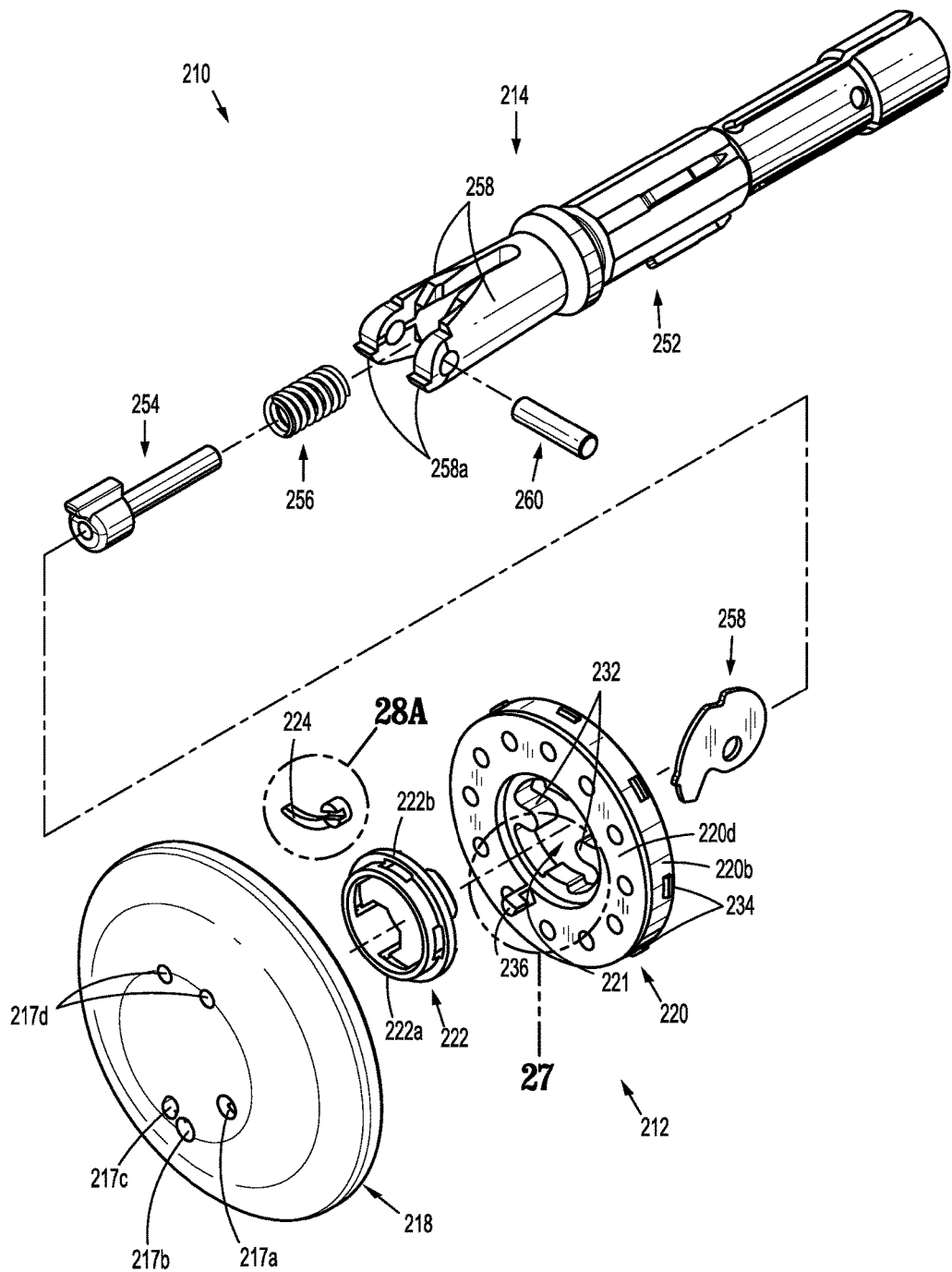
FIG. 26 is a perspective side view of the anvil assembly of FIG. 25 with parts separated.
Figure 27:
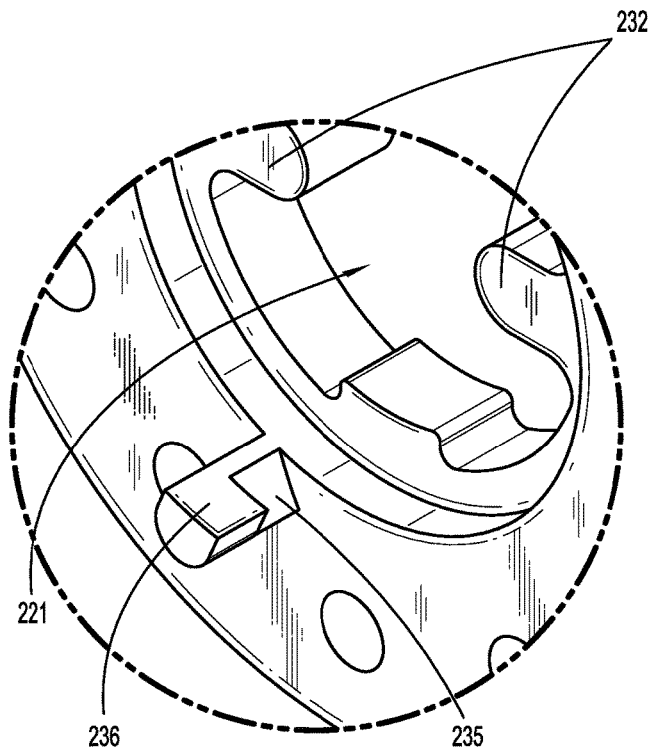
FIG. 27 is an enlarged view of the indicated area of detail shown in FIG. 26.

Referring initially to FIGS. 25-27, the head assembly 212 of the anvil assembly 210 is pivotable relative to the center rod assembly 214 and includes a housing 218, a backup member 220a and cutting ring 220b (collectively, backup member/cutting ring assembly 220), a retainer member assembly 222, and a latch member 224.

With reference to FIGS. 26 and 27, the backup member/cutting ring assembly 220 defines an opening 221 therethrough and includes a pair of inwardly extending fingers 232, a plurality of outwardly extending tabs 234, and a distally extending retaining post 236 defining a cutout 235. The pair of inwardly extending fingers 232 maintains the backup member/cutting ring assembly 220 in rotational alignment with the housing 218 and, when the backup member/cutting ring assembly 220 is in a proximal position, the inwardly extending fingers 232 engage tabs 258a formed on extensions 258 of the center rod 252 of the center rod assembly 214 to maintain the head assembly 212 in the operative position. The plurality of outwardly extending tabs 234 maintain the backup member/cutting ring assembly 220 in a proximal position (FIG. 32) within a cavity 231 of the housing 218.

Figure 34:
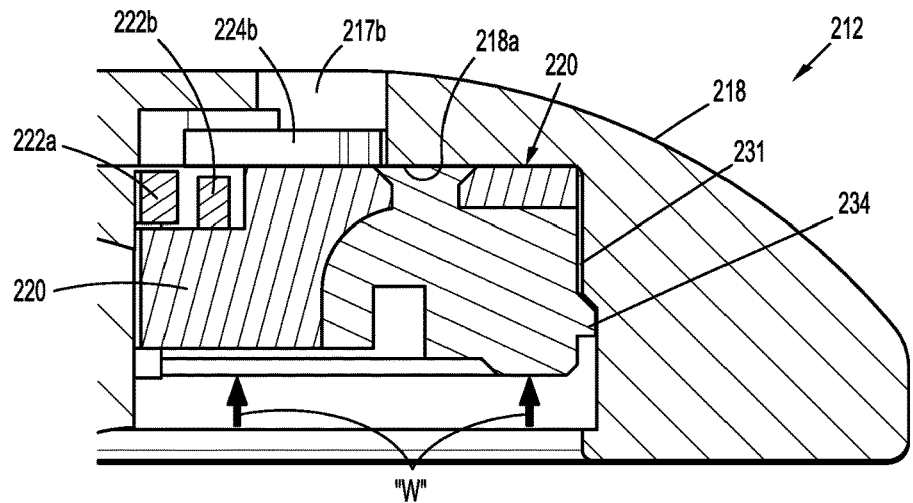
FIG. 34 is a cross-sectional side view taken along line 32-32 shown in FIG. 31 with a backup member/cutting ring assembly in a distal position.
Figure 35:
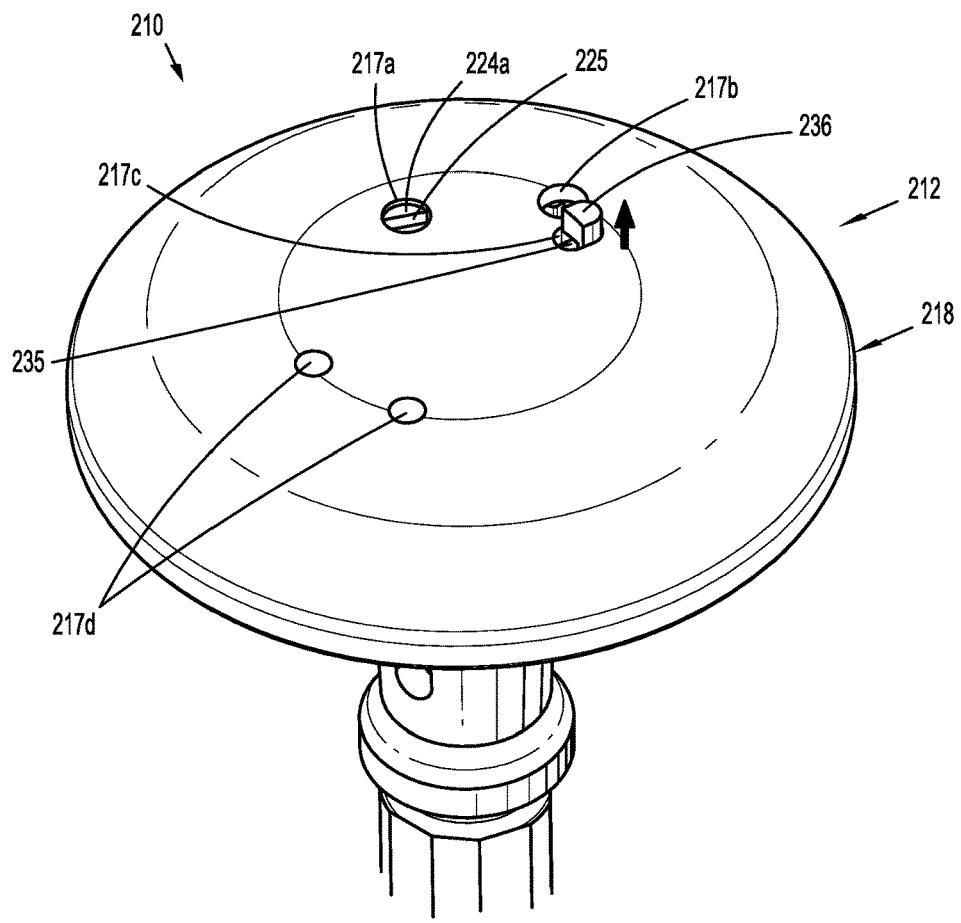
FIG. 35 is a perspective end view of the anvil assembly shown in FIG. 25 in a post fired condition.

As will be described in further detail below, the retaining post 236 maintains the latch member 224 in a first position (FIG. 28) when the anvil assembly 210 is in a pre-fired condition, i.e., the backup member/cutting ring assembly 220 is in the proximal position, and permits the latch member 224 to move to a second position (FIG. 37) when the anvil assembly 210 is in a post fired condition, i.e., the backup member/cutting ring assembly 220 is in a distal position (FIG. 34). Although shown as being integrally formed, the backup member 220a and the cutting ring 220b of the backup member/cutting ring assembly 220 may formed separately and joined together using mechanical fasteners or in any suitable manner.

The retainer member 222 includes a body portion 222a and a frangible ring 222b. The frangible ring 222b maintains the backup member/cutting ring assembly 220 in the proximal position (FIG. 32) until a predetermined force sufficient to fracture or separate the frangible ring 222b from the annular body portion 222a of the retainer member 222 is applied to the backup member/cutting ring assembly 220 by annular knife 33 (FIG. 19) of surgical stapling device 10 (FIG. 1). Fracturing of the frangible ring 222b of the retainer member 222 from the body portion 222a permits movement of the backup member/cutting ring assembly 220 from the proximal position (FIG. 32) to the distal position (FIG. 34).

For a detailed description of the structure and function of exemplary backup member/cutting ring assemblies and retainer members, please refer to commonly owned U.S. application Ser. No. 14/078,766, the content of which is incorporated herein by reference in its entirety.

Figures 28A, 28B:
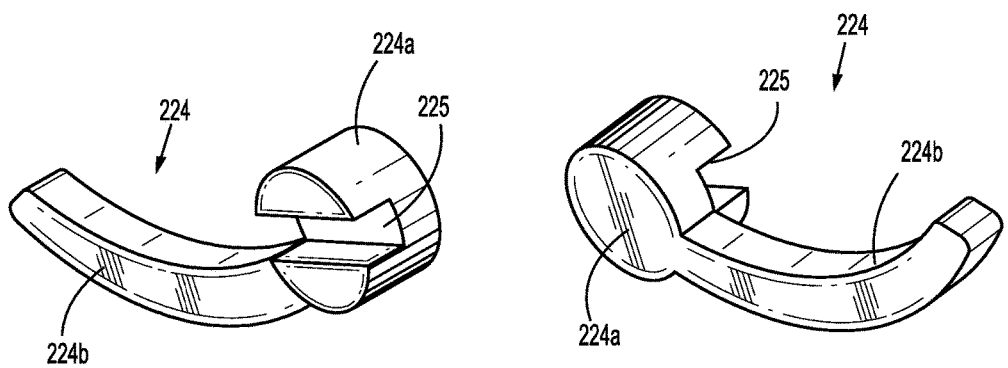
FIGS. 28A and 28B are perspective top and bottom views of a latch member of the anvil assembly shown in FIG. 27.
Figure 37:
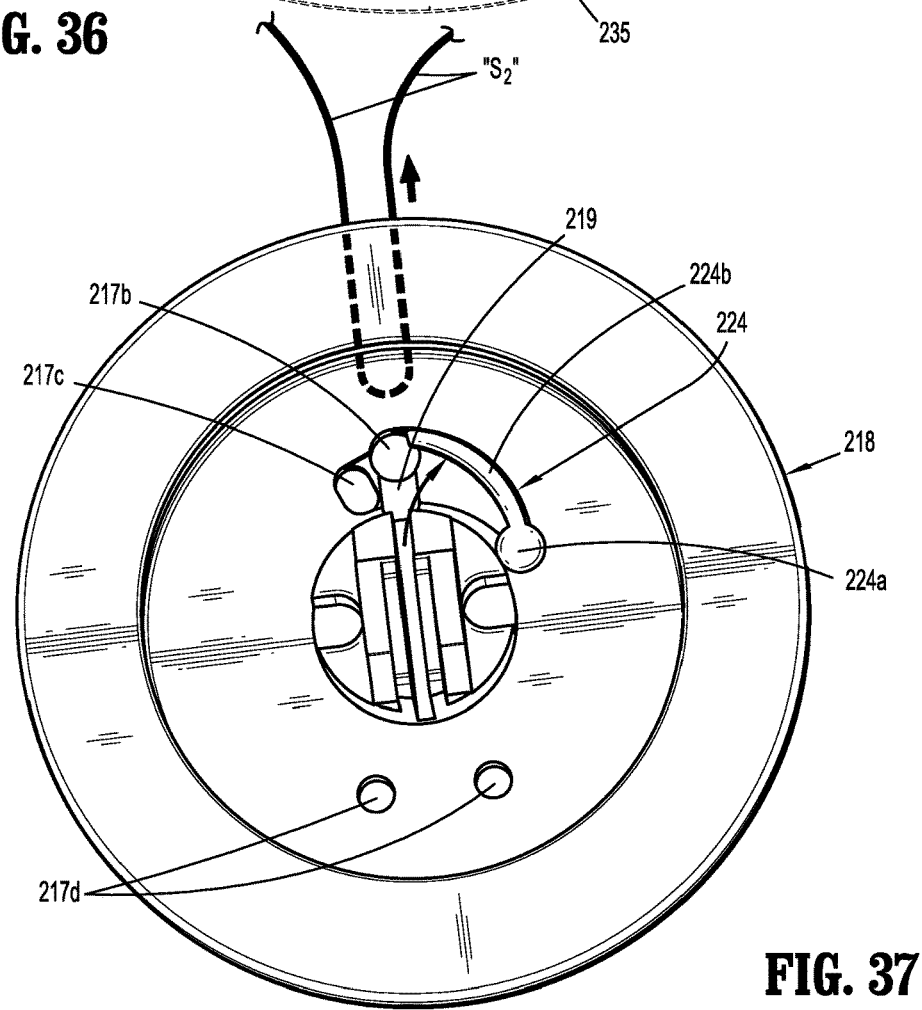
FIG. 37 is a bottom view of the housing and the latch member of the anvil assembly shown in FIG. 25 with the latch member in the second position and a suture being released from the latch member.

Turning briefly to FIGS. 28A and 28B, the latch member 224 includes a first or pivot end 224a and an elongated body portion 224b. As shown, the elongated body portion 224b is curved. The pivot end 224a is substantially cylindrical and is configured to be received within a first opening 217a (FIG. 29) of the housing 218. The elongated body portion 224b is configured to be received within an arcuate recess 215 (FIG. 29) of housing 218. The latch member 224 is configured to be pivoted between a first position (FIG. 30) and a second position (FIG. 37). The pivot end 224a defines a slot 225 (FIG. 28A) configured for engagement by a user to manually pivot the latch member 224 between the first and second positions when the latch member 224 is received within the arcuate recess 215 of the housing 218.

With reference to FIG. 26, the center rod assembly 214 includes a center rod 252, a plunger 254 for engaging the head assembly 212, a plunger spring 256 for biasing the plunger 254 in a distal direction, a cam latch member 258 received within the head assembly 212, and a pivot pin 260 pivotally connecting the head assembly 212 to the center rod 252.

Figure 29:
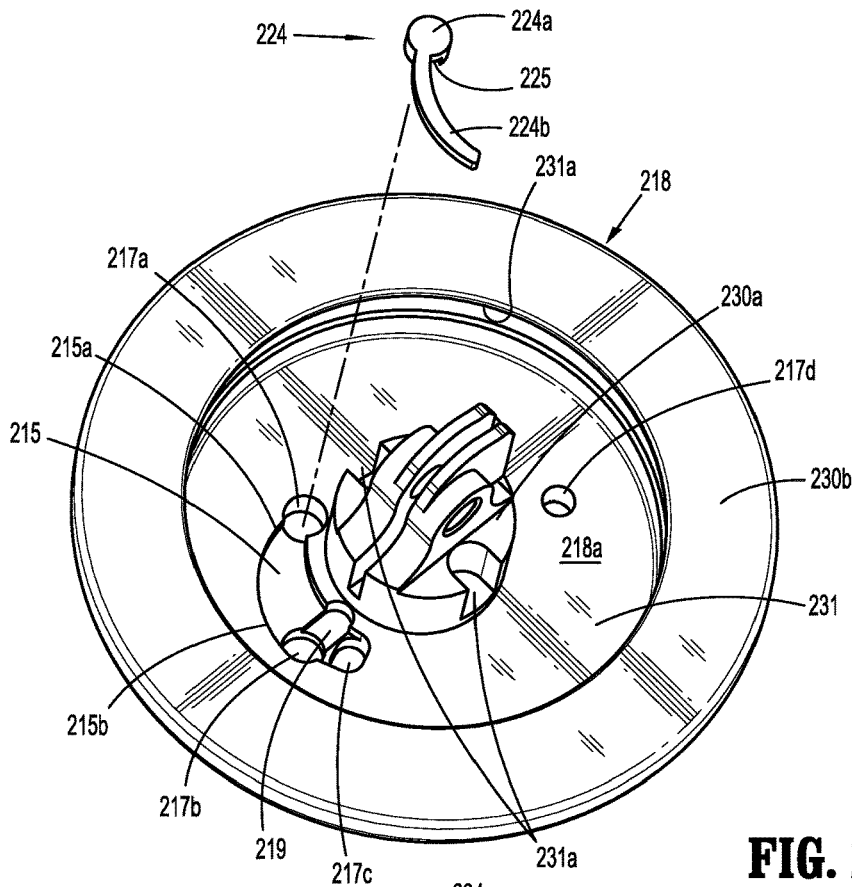
FIG. 29 is an enlarged perspective bottom view of a housing assembly and a latch member of the anvil assembly shown in FIG. 27.
Figure 30:
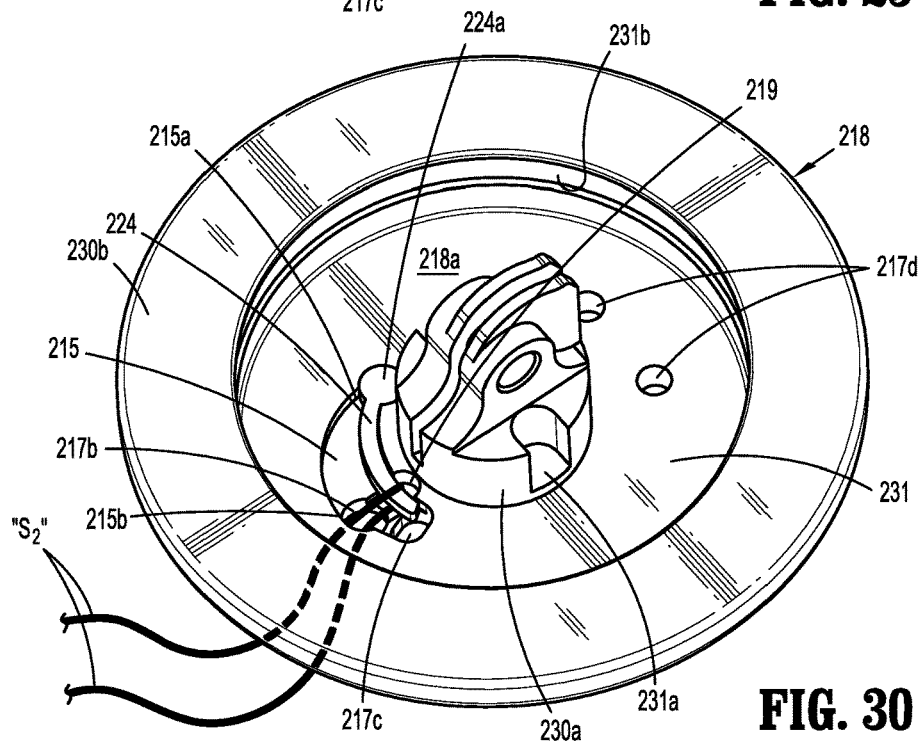
FIG. 30 is a perspective bottom view of the housing and the latch member shown in FIG. 29 with the latch member in a first position.

Referring now to FIGS. 29 and 30, the housing 218 of the head assembly 212 of the anvil assembly 210 includes a center post 230a and an outer rim 230b. The outer rim 230b may include staple forming pockets (not shown). Alternatively, the outer rim 230 is configured to receive an anvil plate (not shown) defining staple forming pockets (not shown). The housing 218 of the head assembly 212 defines a cavity 231 between the center post 230a and the outer rim 230b. The center post 230a defines a pair of recesses 231a for receiving the inwardly extending fingers 232 of the backup member/cutting ring assembly 220. The outer rim 230b defines an annular recess 231b for receiving the plurality of outwardly extending tabs 234 of the backup member/cutting ring assembly 220.

With continued reference to FIGS. 29 and 30, the arcuate recess 215 has a narrow end 215a and a wide end 215b. The arcuate recess 215 is disposed between the center post 230a and the outer rim 230b and operably receives the latch member 224. The housing 218 defines a first opening 217a adjacent the narrow end 215a of the arcuate recess 215 and second and third openings 217b, 217c adjacent the wide end 215b of the arcuate recess 215. The housing 218 further defines a pair of fourth openings 217d on an opposite side of the center post 230a. The inner surface 218a of the housing 218 further defines a cutout 219 in alignment with the second opening 217b for accommodating a second suture "$S_2$" when the second suture "$S_2$" is received about the elongate body portion 224b of the latch member 224 and the latch member 224 is in the first position (FIG. 30) as described in further detail below.

With particular reference to FIG. 30, the first opening 217a pivotally receives the first end 224a of the latch member 224, and the second opening 217b receives the second suture "$S_2$" therethrough. The third opening 217c is configured to receive the retaining post 236 of the cutting ring/retainer member assembly 220 therethrough. The pair of fourth openings 217d is configured to receive the first suture "$S_1$" therethrough, and the cutout 219 accommodates the second suture "$S_2$" when the second suture "$S_2$" is received about the latch member 224.

Figure 31:
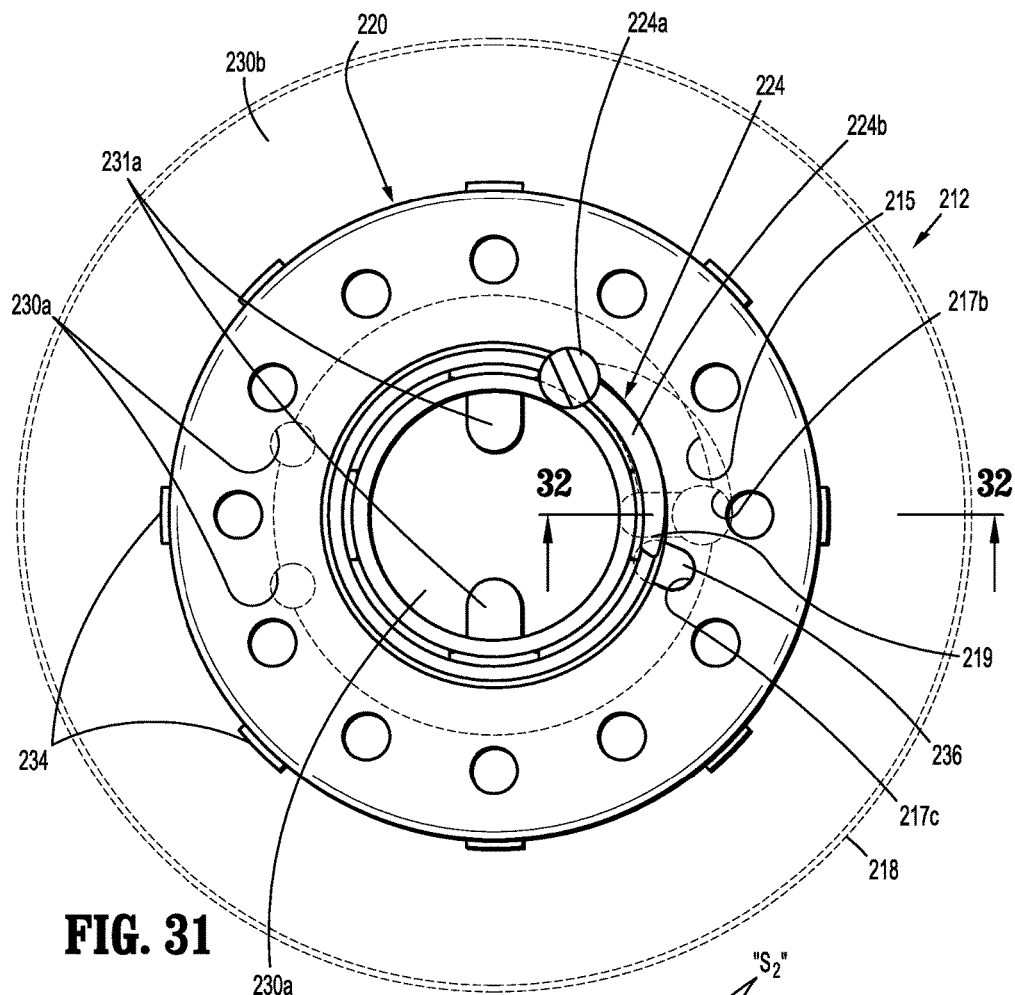
FIG. 31 is an end view of a head assembly of the anvil assembly of FIG. 25 with the housing assembly shown in phantom.
Figure 32:
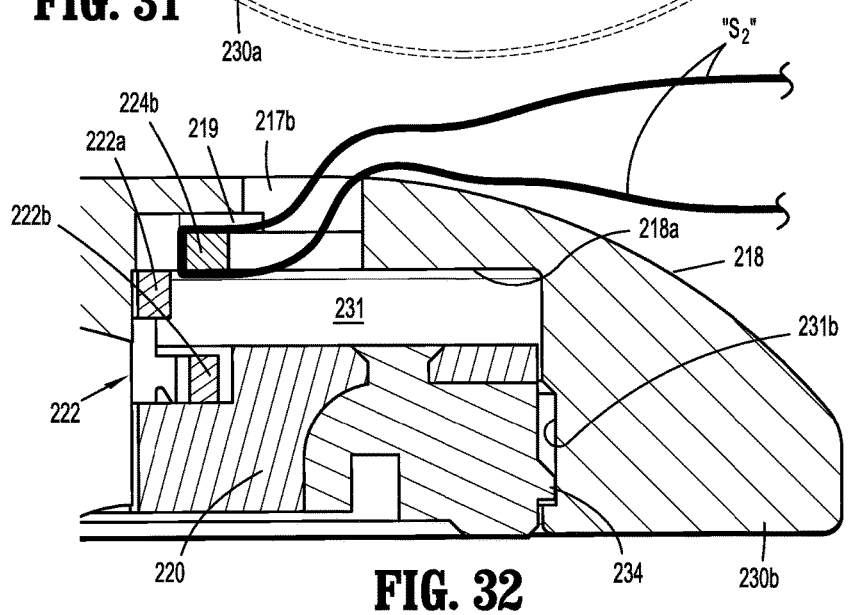
FIG. 32 is a cross-sectional side view taken along line 32-32 shown in FIG. 31 with a backup member/cutting ring assembly in a proximal position.
Figure 33:
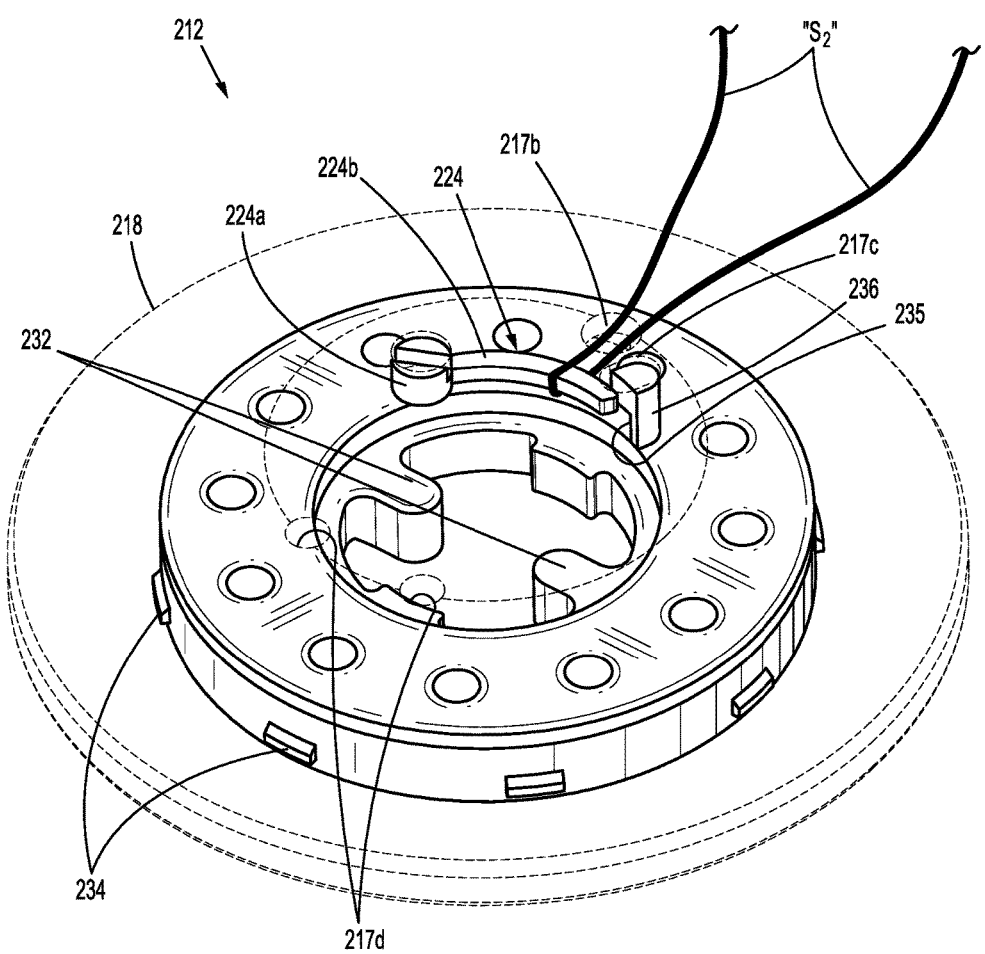
FIG. 33 is a perspective top view of the head assembly shown in FIG. 31 with the housing shown in phantom and the latch member in a first position.

With reference now to FIGS. 31-33, the head assembly 212 of anvil assembly 210 is shown in the pre-fired condition, with the backup member/cutting ring assembly 220 in the proximal position (FIG. 32) and the latch member 224 in the first position (FIG. 33). In the first position of the latch member 224, the elongated body portion 224b of the latch member 224 is positioned to enclose the cutout 219 (FIG. 30). With particular reference to FIG. 32, the backup member/cutting ring assembly 220 is received within the cavity 231 of the housing 218 of the head assembly 212 and the plurality of outwardly extending tabs 234 of the backup member/cutting ring assembly 220 are received within the annular recess 231b of the housing 218. The backup member/cutting ring assembly 220 is maintained within the cavity 231 of the housing 218 through engagement of the plurality of outwardly extending tabs 234 of the backup member/cutting ring assembly 220 with the outer rim 230b of the housing 218.

With continued reference to FIG. 32, the backup member/cutting ring assembly 220 is maintained in the proximal position, i.e., spaced from the inner surface 218a of the housing 218, by the frangible ring 222b of retainer member 222.

In the pre-fired condition, the second suture "$S_2$" is received through the second opening 217b in the housing 218 of the head assembly 212 and about the elongated body portion 224b of the latch member 224. As noted above, the cutout 219 (FIG. 30) in the housing 218 accommodates the second suture "$S_2$" when the latch member 224 is in the first position. As shown in FIG. 30, the second suture "$S_2$" is received within the cutout 219 to prevent the second suture "$S_2$" from sliding off the elongated body portion 224b of the latch member 224 when the latch member 224 is in the first position. Engagement of the retaining post 236 of the backup member/cutting ring assembly 220 by the elongated body portion 224b of the latch member 224 maintains the latch member 224 in the first position.

Turning now to FIGS. 34-37, the anvil assembly 210 is shown with the head assembly 212 in the post-fired condition, with the backup member/cutting ring assembly 220 moved to the distal position (FIG. 34) within the cavity 231 of the housing 218 and the latch member 224 in the second position (FIG. 37). In the second position of the latch member 224, the elongated body portion 224b of the latch member 224 is positioned away from cutout 219 (FIG. 30). As described above, during operation of the surgical stapling device 10 (FIG. 1), the annular knife 33 (FIG. 19) of surgical stapling device 10 is advanced distally into engagement with the backup member/cutting ring assembly 220. With particular reference to FIG. 34, once a predetermined force sufficient to separate the frangible ring 222b of the retainer member 222 is applied to the backup member/cutting ring assembly 220 by the annular knife 33, the frangible ring 222b separates from the body portion 222a of the retainer member 222 and the backup member/cutting ring assembly 220 is advanced within the cavity 231 of the housing 218 towards the inner surface 218a of the housing 218, as indicated by arrows "W".

Figure 36:
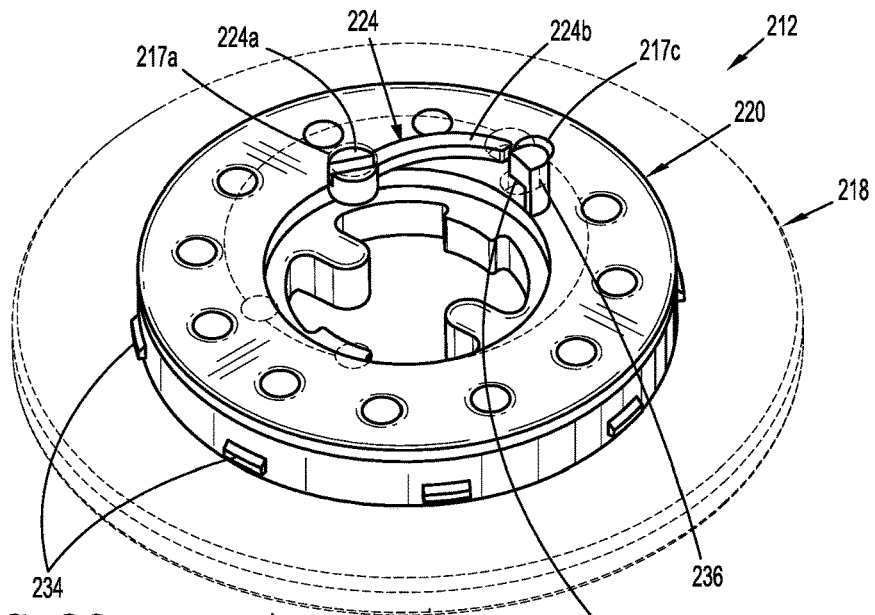
FIG. 36 is a perspective top view of the head assembly shown in FIG. 31 with the housing shown in phantom and the latch member in a second position.

As the backup member/cutting ring assembly 220 advances towards the inner surface 218a of the housing 218 and to the distal position, the retaining post 236 is received through the third opening 217c in the housing 218. With particular reference to FIG. 36, when the backup member/cutting ring assembly 220 is in the distal position, the cutout 235 in the retaining post 236 of the backup member/cutting ring assembly 220 is aligned with the elongated body portion 224b of the latch member 224, thereby freeing the latch member 224 to move to the second position, (FIG. 37). Tension applied to the second suture "S$_2$" causes the latch member 224 to pivot to the second position. Alternatively, the pivot end 224a of the latch member 224 may be engaged by the operator and the latch member 224 may be manually moved to the second position.

With particular reference to FIG. 37, as the latch member 224 moves to the second position in which the latch member 224 no longer encloses the cutout 219. As such, the second suture "S$_2$" is able to slide from about the elongated body portion 224b of the latch member 224 and separate from the latch member 224. Once the second suture "S$_2$" is slid from about the elongated body portion 224b of the latch member 224, the second suture "S$_2$" is retracted through opening 217b in the housing 218 and is detached from the anvil assembly 210.

The anvil assembly 210 may then be separated from the surgical stapling device 10 (FIG. 1) and the surgical procedure may then be completed in in a traditional manner.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
    an anvil center rod;
    a head assembly pivotally secured to the anvil center rod, the head assembly including a housing and a latch member mounted within the housing, the latch member being movable between a first position and a second position; and
    a first suture received about the latch member, wherein in the first position of the latch member the latch member is positioned to prevent release of the first suture from the head assembly and in the second position of the latch member the latch member is positioned to release the first suture from the head assembly.

2. The anvil assembly of claim 1, wherein the head assembly includes a backup member supported within the housing, the backup member being movable within the housing from a proximal position to a distal position.

3. The anvil assembly of claim 2, wherein the backup member includes a retaining post configured to engage the latch member when the backup member is in the proximal position.

4. The anvil assembly of claim 3, wherein the retaining post defines a cutout, the cutout being aligned with the latch member when the backup member is in the distal position.

5. The anvil assembly of claim 1, wherein the latch member includes a curved body portion for receiving the first suture thereabout.

6. The anvil assembly of claim 1, wherein the housing defines an arcuate cutout, the latch member enclosing the cutout when the latch member is in the first position.

7. The anvil assembly of claim 6, wherein the first suture is retained within the cutout when the latch member is in the first position by the latch member.

8. The anvil assembly of claim 2, wherein the head assembly includes a retainer member for maintaining the backup member in the proximal position.

9. The anvil assembly of claim 8, wherein the retainer member includes a body and a frangible ring separable from the body to permit movement of the backup member from the proximal position to the distal position.

10. An anvil assembly comprising:
    an anvil center rod;
    a head assembly pivotally secured to the anvil center rod, the head assembly including a housing and a backup member supported within the housing, the backup member being movable between a proximal position and a distal position; and
    a first suture extending from the head assembly, wherein in the proximal position of the backup member the backup member is positioned to prevent release of the first suture from the head assembly and in the distal position of the backup member the backup member is positioned to release the first suture from the head assembly.

11. The anvil assembly of claim 10, wherein the head assembly includes a latch member mounted within the housing, the latch member being movable within the housing from a first position to a second position.

12. The anvil assembly of claim 11, wherein the backup member includes a retaining post configured to engage the latch member when the backup member is in the proximal position.

13. The anvil assembly of claim 3, wherein the retaining post defines a cutout, the cutout being aligned with the latch member when the backup member is in the distal position.

14. The anvil assembly of claim 2, wherein the latch member includes a curved body portion for receiving the first suture thereabout.

15. The anvil assembly of claim 2, wherein the housing defines an arcuate cutout, the latch member enclosing the cutout when the latch member is in the first position.

16. The anvil assembly of claim 15, wherein the first suture is retained within the cutout when the latch member is in the first position by the latch member.

17. The anvil assembly of claim 10, wherein the head assembly includes a retainer member for maintaining the backup member in the proximal position.

18. The anvil assembly of claim 17, wherein the retainer member includes a body and a frangible ring separable from the body to permit movement of the backup member from the proximal position to the distal position.

* * * * *